US010173209B2

(12) United States Patent
Goussev et al.

(10) Patent No.: US 10,173,209 B2
(45) Date of Patent: Jan. 8, 2019

(54) COMPLEX CATALYSTS BASED ON AMINO-PHOSPHINE LIGANDS FOR HYDROGENATION AND DEHYDROGENATION PROCESSES

(71) Applicants: Dmitri Goussev, Waterloo (CA); Denis Spasyuk, Calgary (CA)

(72) Inventors: Dmitri Goussev, Waterloo (CA); Denis Spasyuk, Calgary (CA)

( * ) Notice: Subject to any disclaimer, the term of this patent is extended or adjusted under 35 U.S.C. 154(b) by 0 days.

(21) Appl. No.: 14/776,947

(22) PCT Filed: Mar. 17, 2014

(86) PCT No.: PCT/CA2014/050280
§ 371 (c)(1),
(2) Date: Sep. 15, 2015

(87) PCT Pub. No.: WO2014/139030
PCT Pub. Date: Sep. 18, 2014

(65) Prior Publication Data
US 2016/0023200 A1 Jan. 28, 2016

Related U.S. Application Data

(60) Provisional application No. 61/792,949, filed on Mar. 15, 2013.

(51) Int. Cl.
| | | |
|---|---|---|
| C07F 15/00 | (2006.01) |
| C07F 9/28 | (2006.01) |
| B01J 31/24 | (2006.01) |
| C07F 9/58 | (2006.01) |
| C07B 31/00 | (2006.01) |
| C07B 33/00 | (2006.01) |
| C01B 3/26 | (2006.01) |
| B01J 31/18 | (2006.01) |
| B01J 31/20 | (2006.01) |
| C07C 29/147 | (2006.01) |
| C07C 37/56 | (2006.01) |

(52) U.S. Cl.
CPC ......... *B01J 31/2461* (2013.01); *B01J 31/189* (2013.01); *B01J 31/1815* (2013.01); *B01J 31/20* (2013.01); *B01J 31/2404* (2013.01); *C01B 3/26* (2013.01); *C07B 31/00* (2013.01); *C07B 33/00* (2013.01); *C07C 29/147* (2013.01); *C07C 37/56* (2013.01); *C07F 9/58* (2013.01); *C07F 15/002* (2013.01); *C07F 15/0046* (2013.01); *B01J 2231/643* (2013.01); *B01J 2231/763* (2013.01); *B01J 2531/0244* (2013.01); *B01J 2531/70* (2013.01); *B01J 2531/821* (2013.01); *B01J 2531/825* (2013.01); *B01J 2531/84* (2013.01); *C01B 2203/1047* (2013.01); *C01B 2203/1076* (2013.01); *C07C 2601/02* (2017.05); *Y02E 60/364* (2013.01)

(58) Field of Classification Search
CPC .... C07F 15/00; C07F 15/002; C07F 15/0046; C07F 9/58; C07F 9/572
USPC .......................... 546/2, 10, 22; 548/101, 112
See application file for complete search history.

(56) References Cited

U.S. PATENT DOCUMENTS

| | | |
|---|---|---|
| 2008/0071121 A1 | 3/2008 | Saudan et al. |
| 2010/0280273 A1 | 11/2010 | Saudan et al. |

FOREIGN PATENT DOCUMENTS

| | | |
|---|---|---|
| JP | 2001/294594 A | 10/2001 |
| WO | 2006/106484 A1 | 10/2006 |
| WO | 2012/052996 A2 | 4/2012 |
| WO | 2013/023307 A1 | 2/2013 |

OTHER PUBLICATIONS

International Search Report issued in corresponding application No. PCT/CA2014/050280 dated Jun. 26, 2014 (3 pages).
Written Opinion of the International Searching Authority issued in corresponding application No. PCT/CA2014/050280 dated Jun. 26, 2014 (5 pages).
International Preliminary Report on Patentability issued in corresponding application No. PCT/CA2014/050280 dated Jun. 12, 2015 (17 pages).
Michael J. Sgro et al., "Oxidative Addition Reactions of Bis-Aminophosphine and Bis-Phosphinite Nickel(0) Pincer Complexes"; Organometallics 2012, 31, 1584-1587 (4 pages).

(Continued)

*Primary Examiner* — Charanjit Aulakh
(74) *Attorney, Agent, or Firm* — Osha Liang LLP

(57) ABSTRACT

The present application discloses novel PWNN and PWNWP metal catalysts for organic chemical syntheses including hydrogenation (reduction) of unsaturated compounds or dehydrogenation of substrates. The range of hydrogenation substrate compounds includes esters, lactones, enals, enones, enolates, oils and fats, resulting in alcohols, enols, diols, and triols as reaction products. The catalysts of current application can be used to catalyze a hydrogenation reaction under solvent free conditions. The present catalysts also allow the hydrogenation to proceed without added base, and it can be used in place of the conventional reduction methods employing hydrides of the main-group elements. Furthermore, the catalysts of the present application can catalyze a dehydrogenation reaction under homogenous and/or acceptorless conditions. As such, the catalysts provided herein can be useful in substantially reducing cost and improving the environmental profile of manufacturing processes for a variety of chemicals.

22 Claims, 5 Drawing Sheets

(56) References Cited

OTHER PUBLICATIONS

Michael J. Sgro et al., "Ni(II), Pd(II) and Pt(II) complexes of PNP and PSP tridentate amino-phosphine ligands"; Dalton Transactions, 2012, 41, 6791-6802 (12 pages).
Feyyaz Durap et al.. "New C2-symmetric chiral phosphinite ligands based on amino alcohol scaffolds and their use in the ruthenium-catalysed asymmetric transfer hydrogenation of aromatic ketones"; Comptes Rendus Chimie publish online Jan. 16, 2013, 16, 363-371 (9 pages).
Duygu Elma et al., "Screening of C2-symmetric chiral phosphnities as ligands for ruthenium(II)-catalyzed asymmetric transfer hydrogenation of prochiral aromatic ketones"; Journal of Organometallic Chemistry, Apr. 1, 2013, 729, 46-52 (7 pages).
Erin A. Gwynne et al., "Nickel(II) and Palladium(II) Bis-Aminophosphine Pincer Complexes"; Organometallics 2011, 30, 4128-4135 (8 pages).
Hiyam Salem et al., "Formation of Stable trans-Dihydride Ruthenium(II) and 16-Electron Ruthenium(0) Complexes Based on Phosphinite PONOP Pincer Ligands. Reactivity toward Water and Electrophiles"; Organometallics 2009, 28, 4791-4806 (16 pages).
Denis Spasyuk et al., "Acceptorless Dehydrogenative Coupling of Ethanol and Hydrogenation of Esters and Imines"; Organometallics 2012, 31, 5239-5242 (4 pages).
Denis Spasyuk et al., "From Esters to Alcohols and Back with Ruthenium and Osmium Catalysts"; Angew. Chem. Int. Ed. 2012, 51, 2772-2775 (4 pages).
Jongwook Choi et al., "Dehydrogenation and Related Reactions Catalyzed by Iridium Pincer Complexes"; Chemical Reviews 2011, 111, 1761-1779 (19 pages).
Osman Dayan et al., "Ruthenium(II) complexes bearing pyridine-based tridentate and bidentate ligands: catalytic activity for transfer hydrogenation of aryl ketones"; Applied Organometallic Chemistry 2012, 26, 663-670 (8 pages).
Bradley George Anderson, "Late Transition Metal Complexes of Pentafluorophenylphosphino-Pincer Ligands"; Victoria University of Wellington 2012 thesis (202 pages).
Response to Written Opinion issued in corresponding application No. PCT/CA2014/050280 dated Feb. 26, 2015.
Saudan, Lionel A., et al., "Dihydrogen Reduction of Carboxylic Esters to Alcohols under the Catalysis of Homogeneous Ruthenium Complexes: High Efficiency and Unprecedented Chemoselectivity"; Angew. Chem. Int. Ed., vol. 46, 2007; Wiley—DOI: 10.1002/anie.200701015; pp. 7473-7476.
Patchett, Ruth, et al., "Asymmetric Hydrogenation of Ketones with H2 and Ruthenium Catalysts Containing Chiral Tetradentate S2N2 Ligands"; Angew. Chem. Int. Ed., vol. 52, 2013; Wiley—DOI: 10.1002/anie.201304844; pp. 10352-10355.
Sheldon, Roger A., "Fundamentals of green chemistry: efficiency in reaction design"; Chem. Soc. Rev., vol. 41, 2012, published by the Royal Society of Chemistry; pp. 1437-1451.
Morton, David, et al., "Hydrogen Production from Ethanol catalysed by Group 8 Metal Complexes"; J. Chem. Soc. Dalton Trans. (1989); published on Jan. 1, 1989; downloaded by Johnson Matthey on Feb. 20, 2017; pp. 489-495.
Morton, David, et al., "Molecular Hydrogen Complexes in Catalysis: Highly Efficient Hydrogen Production from Alcoholic Substrates catalysed by Ruthenium Complexes"; J. Chem. Soc., Chem. Commun., 1988; published on Jan. 1, 1988; downloaded by Johnson Matthey on Feb. 20, 2017; pp. 1154-1156.
Morton, David, et al., "Rapid Thermal Hydrogen Production from Alcohols catalysed by [Rh(2,2'-bipyridyl)2]Cl"; J. Chem. Soc., Chem. Commun., 1987; published on Jan. 1, 1987; downloaded by Johnson Matthey on Feb. 20, 2017; pp. 248-249.
Milstein, David, "Discovery of Environmentally Benign Catalytic Reactions of Alcohols Catalyzed by Pyridine-Based Pincer Ru Complexes Based on Metal-Ligand Cooperation";Top Catal, vol. 53 (2010); DOI: 10.1007/s11244-010-9523-7; pp. 915-923.
Nielsen, Martin, et al., "Towards a Green Process for Bulk-Scale Synthesis of Ethyl Acetate: Efficient Acceptorless Dehydrogenation of Ethanol"; Angew. Chem. Int. Ed., vol. 51 (2012); Wiley—DOI: 10.1002/anie.201200625; pp. 5711-5713.
Gusev, Dmitry G., et al., "Cyclometalated Osmium Complexes Containing a Tridentate PCP Ligand"; Organometallics, vol. 20 (2001); American Chemical Society 2001 10.1021/0m000823x, published on Web Feb. 1, 2001; pp. 1001-1007.
Spasyuk, Denis, et al., "From Esters to Alcohols and Back with Ruthenium and Osmium Catalysts"; Angew. Chem. Int. Ed., vol. 51 (2012); Wiley—DOI: 10.1002/anie.201108956; pp. 2772-2775.
Köllhofer, Axel, et al., "Homogeneous Catalysts Supported on Soluble Polymers: Biphasic Sonogashira Coupling of Aryl Halides and Acetylenes Using MeOPEG-Bound Phosphine—Palladium Catalysts for Efficient Catalyst Recycling"; Chem. Eur. J., vol. 9, No. 6, 2003; Wiley—0947-6539/03/0906-1416; pp. 1416-1425.
Goerlich, Jens R., et al., "Organophosphorus Compounds With Tertiary Alkyl Substituents. VI1: A Convenient Method for the Preparation of DI-1-Adamantylphosphine and DI-1-adamantylphosphine"; Phosphorus, Sulfur, and Silicon and the Related Elements, 102:1-4, DOI: 10.1080/10426509508042559 (http://dx.doi.org/10.1080/10426509508042559, published online: Oct. 4, 2006); pp. 211-215.
Castarlenas, Ricardo, et al., "N-Heterocyclic Carbene—Osmium Complexes for olefin Metathesis Reactions"; Organometallics, vol. 24, 2005; 2005 American Chemical Society published on web Jul. 23, 2005, 10.1021/om050569e; pp. 4343-4346.
Michael J. Sgro et al: "Synthesis and reactivity of ruthenium tridentate bis-phosphinite ligand complexes", Dalton Transactions: The International Journal for Inorganic, Organometallic and Bioinorganic Chemistry, vol. 42, No. 29, May 31, 2013, pp. 10460-10472, XP055319195, GB ISSN: 1477-9226, DOI: 10.1039/c3dt51065d Scheme 3, complexes 15 and 6 abstract (13 pages).
Jing Zhang et al: "Electron—Rich PNP—and PNN—Type Ruthenium (II) Hydrido Borohydride Pincer Complexes. Synthesis, Structure, and Catalytic Dehydrogenation of Alcohols and Hydrogenation of Esters", Organometallics, vol. 30, No. 21, Nov. 14, 2011, pp. 5716-5724, XP055030403, ISSN: 0276-7333, DOI: 10.1021/om200595m Figure 1, complexes 1 and 2 Scheme 4, complexes 8 and 9 tables 2,3 (9 pages).
Extended European Search Report issued in European Patent Application No. 14765683.9; dated Nov. 22, 2016 (9 pages).
Powell, John, et al., Synthesis of Group 6 Metalla-(Aza)-Crown Ether Tetracarbonyl Complexes with Potentially Anionic Amido Groups. The Influence of Li+, Mg2+, and Al3+ Cations on the Susceptibility of the Carbonyl Ligand to Nucleophillic Addition of Alkyl/Aryl Carbanions and Hydride; Organometallics 1989, 8; pp. 2942-2947.
Bendayan, Andree, et al., "Synthese De Ligands De Type Amino—Diphosphinites; Etude En RMN 13C ET 31P. Application A I.A. Dimerisation Du Butadiene Par Les Complexes Du Nickel"; Journal of Organometallic Chemistry, 326 (1987); pp. 289-297.

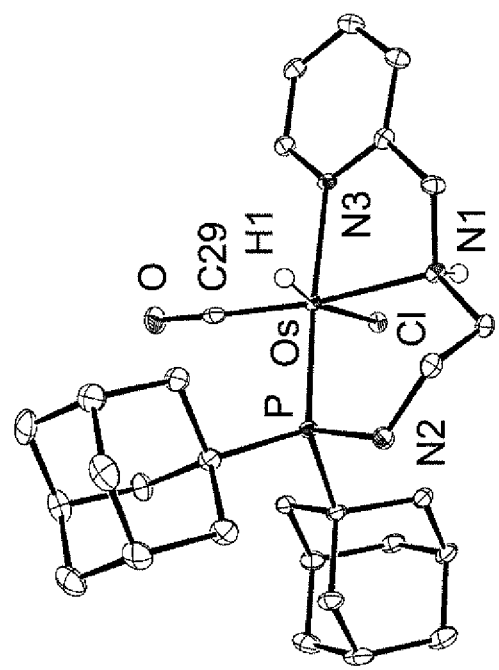
FIGURE 3
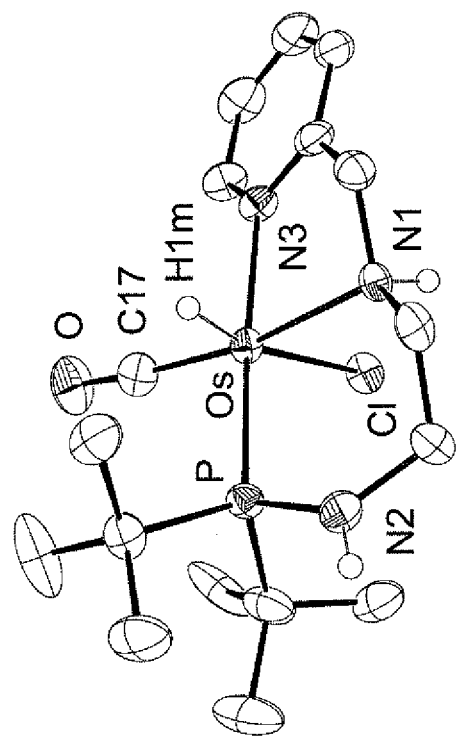

COMPLEX CATALYSTS BASED ON AMINO-PHOSPHINE LIGANDS FOR HYDROGENATION AND DEHYDROGENATION PROCESSES

RELATED APPLICATION

This application is a National Stage Entry of PCT/CA2014/050280, filed on Mar. 17, 2014, which claims priority to U.S. Provisional PATENT Application No. 61/792,949 filed on Mar. 15, 2013, the contents of which are incorporated herein by reference in its entirety.

FIELD OF THE INVENTION

The present invention pertains to catalysts. More specifically, the present invention pertains to catalysts useful in hydrogenation and dehydrogenation reactions.

INTRODUCTION

Reduction of polar C=X (where X is O or N) bonds is one of the most fundamental organic reactions and is useful for the synthesis of a variety of organic alcohols and amines. Reduction of esters and imines is typically accomplished using main-group hydride reagents, such as $LiAlH_4$, or using molecular hydrogen. The use of the hydride reducing reagents is inconvenient and expensive, particularly on a large scale; furthermore, this approach generates large amounts of chemical waste. The hydride reduction method can be dangerously exothermic at the stage of quenching and can be difficult to control. Consequently, catalytic reduction of esters under hydrogen gas is, comparatively, a possible 'green' alternative to the classical hydride reduction.

A key aspect of the ester reduction with molecular hydrogen is the catalytic system utilized in the process that can rapidly bind and split molecular hydrogen to give a transition-metal hydride. The development of highly efficient and useful catalysts and catalytic systems for hydrogenation of lactones, esters, oils, and fats is an important, but currently unmet, need in chemistry. Of particular interest is the development of hydrogenation processes that operate in the temperature range of 20 to 100° C. and use less than 500 ppm (0.05 mol %) catalyst under relatively low $H_2$ pressure (1-50 bar). Among the few catalysts and catalytic systems capable of converting esters and lactones into alcohols and diols under hydrogen gas, presently most useful and efficient are complexes of ruthenium with bidentate phosphine-amine and tetradentate phosphine-imine ligands (described in Publication No. US 2010/0280273 A1, WO 2012/052996 A2, and in *Angew. Chem. Int. Ed.* 2007, 46, 7473, each of which is incorporated herein by reference in its entirety). These references describe ruthenium catalyst loadings of 500-1000 ppm (0.05-0.1 mol %), however, the disclosed methods suffer from relatively poor efficiency (low turnover numbers even at 100-110° C.) and often require a large amount of base (5-10 mol %), such as NaOMe, thereby reducing the product selectivity and generating large amounts of chemical waste (due to the need for product neutralization and extensive purification).

Additionally, development of robust $H_2$ hydrogenation catalysts with high carbonyl selectivity has been a long-standing challenge, especially for applications with low catalyst loadings (e.g., substrate-to-metal ratios in excess of $10^3$). Certain types of unsaturated carbonyls (see FIG. 1) are particularly vulnerable to C=C bond hydrogenation and isomerization under the catalytic conditions. Unfortunately, many precursors to commercially important synthetic and natural chemicals, flavour and fragrances, and unsaturated fatty acid derivatives of plant oils, are susceptible to such non-specific C=C bond hydrogenation and isomerization.

In the 90's, Noyori and co-workers discovered an efficient catalytic system for the chemoselective hydrogenation of enals and enones, comprising a six-coordinate $RuCl_2P_2N_2$ species containing two phosphorus and two nitrogen donors, applied in basic 2-propanol. There has subsequently been a sustained research effort aimed at exploring the Noyori-type Ru(II) catalysts with N and P donors in varied combinations as bidentate, tridentate, and tetradentate ligands. Very recently, this research has been successfully extended to Ru(II) chloride complexes with tetradentate aminothioether (SNNS) ligands (R. Patchett, I. Magpantay, L. Saudan, C. Schotes, A. Mezzetti, F. Santoro, *Angew. Chem. Int. Ed.* 2013, 52, 10352-10355, incorporated herein by reference in its entirety).

Chemoselectivity is even more difficult to achieve in the hydrogenation of esters, which is a challenging reaction by itself, where few efficient catalysts are known and have only become available in recent years: Milstein's Ru-PNN catalyst (catalyst I, FIG. 2); industrial Ru-PN, PNP, PNNP catalysts (catalysts II, III, IV, FIG. 2), and Gusev's Os-PNN catalyst (catalyst V, FIG. 2). The development of additional and/or improved highly selective catalysts and catalytic systems for hydrogenation of unsaturated carbonyls remains an important need in chemistry (R. A. Sheldon, *Chem. Soc. Rev.* 2012, 41, 1437-1451).

The development of green chemical processes and the use of biomass for hydrogen production have attracted much attention in recent years. Furthermore, acceptorless dehydrogenative coupling of primary alcohols is an interesting transformation that produces esters, imines, amines, or amides. Oxidant-free, catalytic dehydrogenation of alcohols is of great importance for the chemical industry. A significant progress in dehydrogenation of bio-alcohols (chiefly ethanol) has been achieved with heterogeneous catalysts, however, at the cost of using drastic reaction conditions: high temperature (>200° C.) and pressure. Therefore, designing well-defined homogeneous catalysts for alcohol dehydrogenation under mild conditions represents an important scientific and practical goal. There has been little progress in the area of acceptorless dehydrogenation of primary alcohols since Cole-Hamilton and co-workers demonstrated dehydrogenation of ethanol catalyzed by $[RuH_2(N_2)(PPh_3)_3]$, where an excess of NaOH, high temperature (150° C.), and an intense light source were needed to achieve TOF=210 $h^{-1}$, after 2 h (D. Morton, D. J. Cole-Hamilton, I. D. Utuk, M. Paneque-Sosa, M. Lopez-Poveda, *J. Chem. Soc. Dalton Trans.* 1989, 489; D. Morton, D. Cole-Hamilton, *J. Chem. Soc. Chem. Commun.* 1988, 1154; and D. Morton, D. J. Cole-Hamilton, *J. Chem. Soc. Chem. Commun.* 1987, 248). In recent years, outside of the work of the present inventors, few homogeneous catalysts for acceptorless dehydrogenative coupling of primary alcohols have been developed and studied, such as the systems published by Milstein and co-workers (for a review see: D. Milstein, *Top. Catal.* 2010, 53, 915) and Beller (*Angew. Chem., Int. Ed.* 2012, 51, 5711). However, most of these catalysts, with the exception of Ru-MACHO, are inactive at temperatures below 100° C., for example, for converting ethanol and propanol to hydrogen and ethyl acetate and propyl propionate, respectively.

Therefore, there remains a need for efficient and practical metal catalysts for hydrogenation of, for example, esters, lactones, and fats and oils derived from natural sources, which could operate under base-free conditions using relatively low reaction temperature and hydrogen pressure. Additionally, there remains a need for catalysts and catalyst systems that can chemoselectively hydrogenate carbonyl functionalities of unsaturated carbonyl compounds. There also remains a need for practical catalysts capable of efficient alcohol dehydrogenation under mild, and preferably neutral, reaction conditions, for environmentally benign production of esters and lactones from alcohols and diols, accompanied by formation of hydrogen gas.

The above information is provided for the purpose of making known the data believed by the applicant to be of possible relevance to the present invention. No admission is necessarily intended, nor should be construed, that any of the preceding information constitutes prior art against the present invention.

SUMMARY OF THE INVENTION

An object of the present invention is to provide catalytic complexes that are useful for regioselective, chemoselective, and/or stereoselective hydrogenations and/or dehydrogenations. It is another object of the present invention to provide metal complexes containing P-W-N-W' ligands useful for catalytic hydrogenation of esters, ketones, enals, enones, enoates, plant and seed oils, esters with multiple ester groups and imines, and for catalytic dehydrogenation of alcohols and amines.

In accordance with one aspect of the application, there is provided a compound of Formula A

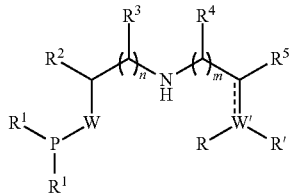

Formula A wherein
each $R^1$, $R^2$, $R^3$, and $R^4$ are each independently H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, or when taken together with the atoms to which they are attached, any two of the $R^2$, $R^3$, $R^4$ groups form an optionally substituted saturated or partially saturated cycloalkyl, or an optionally substituted aryl or heteroaryl;
W is an oxygen atom or an NH group;
W' is an oxygen atom or a nitrogen atom;
the dashed line is either present and denotes the presence of one bond of a double bond or is absent;
R is absent, H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group;
R' is H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, $PR_2$ or, when taken together with $R^5$ and the atoms to which they are attached forms a substituted or unsubstituted heteroaryl; and
n and m are each independently an integer 1 or 2.

In accordance with one embodiment, there is provided a compound of Formula (A), wherein when R' is $PR_2$, R is H, or, when $R^5$ and R' do not form part of a heteroaryl, $R^5$ is H. In accordance with another embodiment, there is provided a compound of Formula (A), wherein R' taken together with $R^5$ and the atoms to which they are attached forms a substituted or unsubstituted heteroaryl, such as pyridyl, furanyl, imidazolyl, pyrazolyl or oxazolyl.

In accordance with another embodiment, there is provided a compound which has the structure of Formulae Ia, Ib, or Ic,

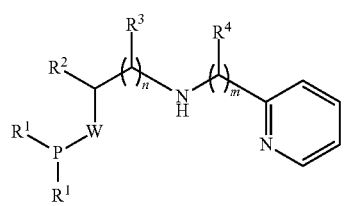

Formula Ia

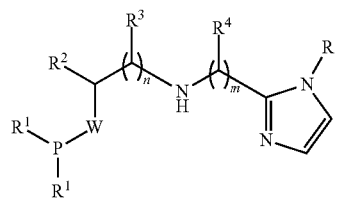

Formula Ib

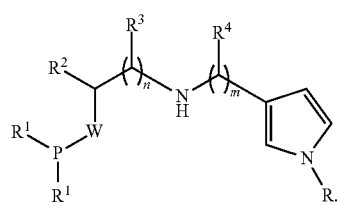

Formula Ic

In accordance with another embodiment, there is provided compounds of formulae (A), (Ia), (Ib), and (Ic), wherein n is 1, or m is 1 or both n and m are 1.

In accordance with another embodiment, there is provided a compound which has the structure of Formula I, Formula II or Formula III,

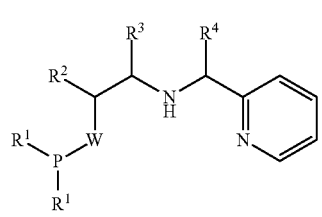

Formula I

-continued

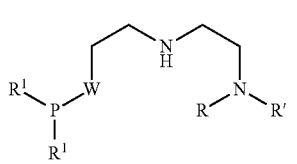
Formula II

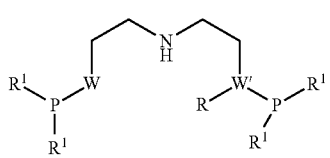
Formula III wherein in Formula II, R is not absent and in Formula III, W' is an oxygen atom and R is absent or W' is a nitrogen atom and R is H.

In accordance with another embodiment, there is provided a compound of Formulae (A), (Ia), (Ib), (Ic), (I), (II), and (III) that is coordinated to a transition metal, which is, optionally, of group 7 (manganese group), a group 8 (iron group), group 9 (cobalt group), or group 10 (nickel group), and is preferably Ru or Os.

In accordance with another aspect, there is provided a metal complex of Formulae IV or V $$M(PWNN)X_kY \qquad (IV)$$

$$M(PWNWP)X_kY \qquad (V)$$

wherein M is a transition metal;
each X represents simultaneously or independently a hydrogen or a halogen atom, a $C_1$-$C_5$ alkyl radical, a hydroxyl group, or a $C_1$-$C_7$ alkoxy radical;
Y is CO, NO, carbene, isonitrile, nitrile, phosphite, phosphinite, or a phosphine, such as $PMe_3$, $PPh_3$, $PCy_3$, $P(iPr)_3$;
k is an integer 1 or 2; and
PWNN and PWNWP are ligands represented by Formula A

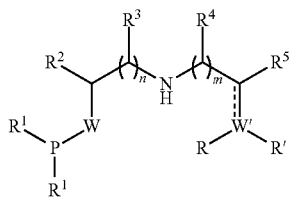
Formula A wherein
each $R^1$, $R^2$, $R^3$, and $R^4$ are each independently H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, or when taken together with the atoms to which they are attached, any two of the $R^2$, $R^3$, $R^4$ groups form an optionally substituted saturated or partially saturated cycloalkyl, or an optionally substituted aryl or heteroaryl;
W is an oxygen atom or an NH group;
W' is an oxygen or a nitrogen atom;
the dashed line is either present and denotes the presence of one bond of a double bond or is absent;
R is absent, H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group;
R' is H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, $PR_2$ or, when taken together with $R^5$ and the atoms to which they are attached forms a substituted or unsubstituted heteroaryl; and
n and m are each independently an integer 1 or 2
wherein in the PWNN ligand W' is a nitrogen atom and in the PWNWP ligand W' is an oxygen or a nitrogen atom and R' is $PR_2$, and
wherein the metal complex of Formulae IV or V is either neutral or cationic.

In accordance with another embodiment, there is provided a metal complex of formula (IV) or (V) which comprises the PWNN ligand wherein R' taken together with $R^5$ and the atoms to which they are attached forms a substituted or unsubstituted heteroaryl, such as pyridyl, furanyl, imidazolyl, pyrazolyl or oxazolyl.

In accordance with another embodiment, there is provided a metal complex of formula (IV) or (V), wherein the PWNN ligand has the structure of Formula Ia, Ib, or Ic,

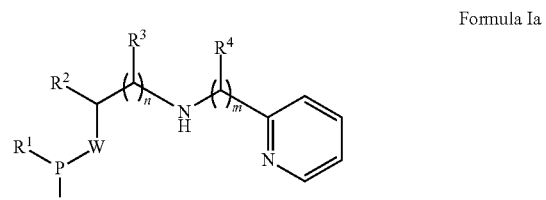
Formula Ia

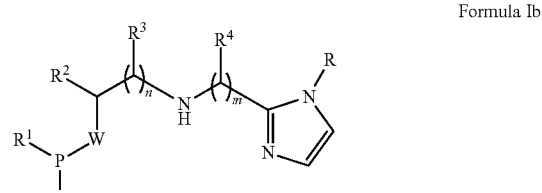
Formula Ib

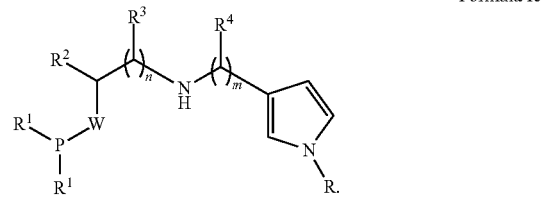
Formula Ic

In accordance with another embodiment, there is provided a metal complex of formula (IV) or (V), with compounds of formulae (A), (Ia), (Ib), and/or (Ic), wherein n is 1, or m is 1 or both n and m are 1.

In accordance with another embodiment, there is provided a metal complex of formula (IV) or (V), which comprises a PWNN ligand having the structure of Formula I or Formula II,

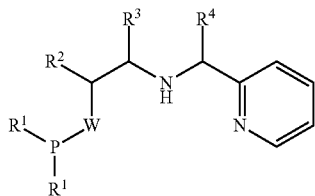

Formula I

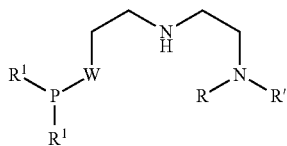

Formula II wherein in Formula II, R is not absent; or
a PWNWP ligand and has the structure of Formula III,

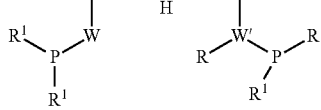

Formula III wherein when W' is an oxygen atom R is absent and when W' is a nitrogen atom R is H.

In accordance with another embodiment, there is provided a metal complex of formula (IV) or (V), wherein M is a group 7 (manganese group) metal, a group 8 (iron group) metal, group 9 (cobalt group) metal, or group 10 (nickel group) metal; preferably, M is is Ru or Os.

In accordance with another embodiment, there are provided metal complexes of Formula (IV) or (V) having the following structures:

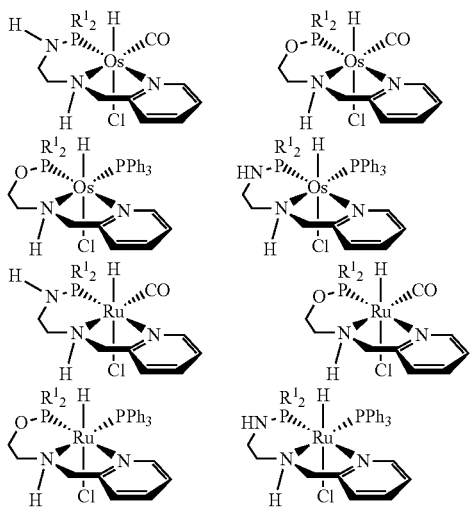

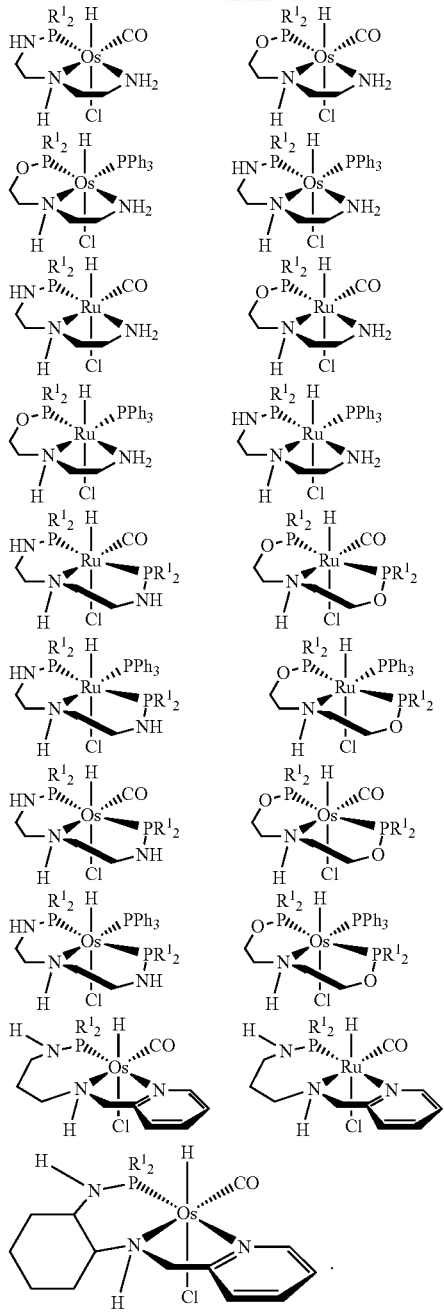

In accordance with another aspect, there is provided a process for dehydrogenation of a substrate, comprising treating the substrate with a catalytic amount of any one of the herein described metal complexes.

In accordance with another embodiment, there is provided a process for dehydrogenation, wherein the substrate is treated with the catalytic amount of the metal complex in the presence of a base, a solvent or both, and/or at a reaction temperature between about 0° C. and about 250° C. or between about 50° C. and about 150° C., or between about 50° C. and about 100° C., or between about 50° C. and about 75° C.

In accordance with another embodiment, there is provided a process for dehydrogenation, wherein the substrate has at least one alcohol moiety; or, optionally, is a compound of the following formula:

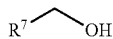

wherein $R^7$ is a substituted or unsubstituted alkyl or a substituted or unsubstituted aryl; or comprises an amino group that undergoes dehydrogenation.

In accordance with another embodiment, there is provided a process for dehydrogenation, wherein the substrate comprises more than one hydroxyl moiety that undergoes dehydrogenation.

In accordance with another embodiment, there is provided a process for dehydrogenation, wherein the substrate and product pair of the dehydrogenation reaction is selected from the group consisting of:

| Substrate | Product |
|---|---|
| Alcohols | ester |
| Alcohol | aldehyde |
| Alcohol | ketone |
| Diol | lactone |
| amine + alcohol | amide |
| amine + alcohol | substituted amine |
| amine + alcohol | imine |
| ammonia-borane | aminoboranes |
| ammonia-borane | borazine |
| Amine | imine |
| Amines | guanidine |
| alcohol + thiol | thioester |
| Thiol | sulphoxide |
| alcohol + phosphine | acyl phosphine |

In accordance with another embodiment, there is provided a process for dehydrogenation, wherein the catalytic amount of metal complex is between 10-1000 pm, or between 10-500 ppm, or between 10-250 ppm, or between 10-100 ppm, or between 10-50 ppm.

In accordance with another embodiment, there is provided a process for dehydrogenation, utilized for producing $H_2$.

In accordance with another aspect, there is provided a process for producing $H_2$ comprising dehydrogenating a substrate by treating the substrate with a catalytic amount of any one of the aforementioned metal complexes.

In accordance with another embodiment, there is provided a process for producing $H_2$, wherein the substrate comprises an alcohol or amine or wherein the substrate is ammonia-borane.

In accordance with another embodiment, there is provided a process for producing $H_2$, wherein the process does not require a hydrogen acceptor; and/or is a homogeneous process.

In accordance with another aspect, there is provided a process for hydrogenation of a substrate comprising treating the substrate under a pressure of hydrogen with a catalytic amount of any one of the herein described metal complexes.

In accordance with another embodiment, there is provided a process for hydrogenation, wherein the substrate is treated with the catalytic amount of the metal complex in the presence of a base, a solvent or both; and/or at a reaction temperature between about 0° C. and about 200° C., or between about 20° C. and about 100° C., or between about 20° C. and about 75° C., or between about 20° and about 50° C.

In accordance with another embodiment, there is provided a process for hydrogenation, wherein the substrate has at least one ester, enal, enone, or enolate moiety.

In accordance with another embodiment, there is provided a process for hydrogenation, which proceeds according to one of the following schemes:

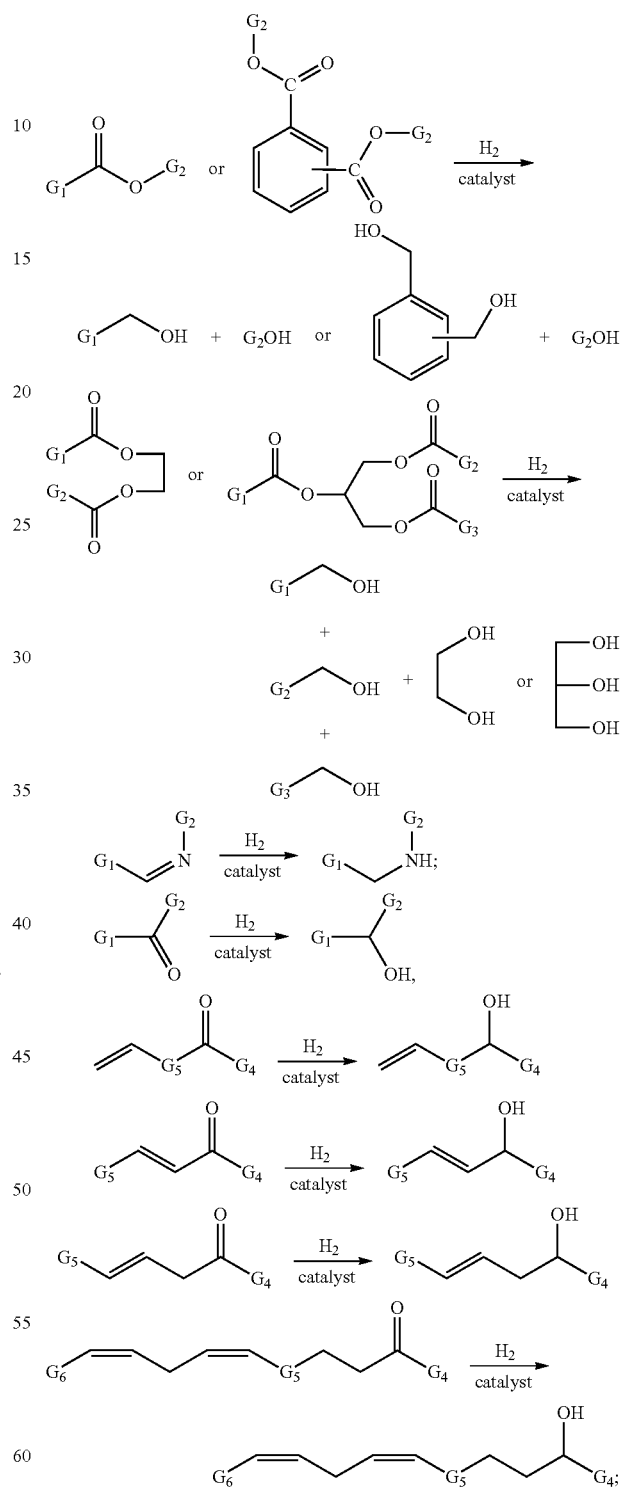

wherein groups $G_1$, $G_2$, and $G_3$ simultaneously or independently, represent a linear, branched $C_1$-$C_{40}$ or cyclic $C_3$-$C_{40}$ alkyl, alkenyl or aromatic group, optionally substituted.

In accordance with another embodiment, there is provided a process for hydrogenation, wherein the substrate and product pair of the hydrogenation reaction is selected from the group consisting of:

| Hydrogenation Substrate | Product |
| --- | --- |
| Aldehyde | alcohol |
| Ketone | alcohol |
| Ester | alcohol |
| carboxylic acid | alcohol |
| Ketene | alcohol |
| Enol | alcohol |
| Epoxide | alcohol |
| Aldimine | amine |
| Ketamine | amine |
| ketene-imine | amine |
| Nitrile | amine |
| Aziridine | amine |
| Nitro | amine |
| Diazo | amine |
| Isocyanide | amine |
| Enamine | amine |
| Lactone | diol |
| Amide | amine + alcohol |
| Aminoboranes | amine-borane |
| Borazine | amine-borane |
| Olefin | alkane |
| Acetylene | alkane |
| Allene | alkane |

In accordance with another embodiment, there is provided a process for hydrogenation, wherein the catalytic amount of metal complex is between about 10 and about 1000 pm, or between about 10 and about 500 ppm, or between about 10 and about 250 ppm, or between about 10 and about 100 ppm, or between about 10 and about 50 ppm.

In accordance with another embodiment, there is provided a process for hydrogenation, wherein the hydrogen pressure is between about 1 and about 200 bar, or between about 1 and about 150 bar, or between about 1 and about 100 bar, or between about 1 and about 70 bar, or between about 1 and about 50 bar.

In accordance with another embodiment, there is provided a process for hydrogenation, wherein the hydrogenation proceeds regioselectively, chemoselectively, and/or stereoselectively.

In accordance with another embodiment, there is provided processes for dehydrogenation, $H_2$ production, and/or hydrogenation, wherein the process is performed in the absence of solvent, base or both.

BRIEF DESCRIPTION OF THE FIGURES

For a better understanding of the invention and to show more clearly how it may be carried into effect, reference will now be made by way of example to the accompanying drawings, which illustrate aspects and features according to embodiments of the present invention, and in which:

FIG. 3 depicts ORTEP plots of complex 3 (left) and 4 (right). Thermal ellipsoids are at 50% and most hydrogen atoms are not shown for clarity;

DESCRIPTION OF THE INVENTION

Definitions

Figure 1:
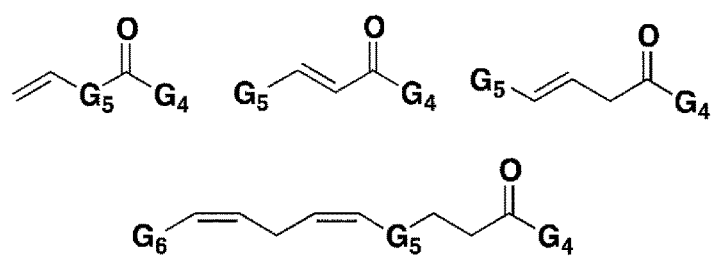
FIG. 1 depicts examples of unsaturated carbonyl compounds, wherein $G_{4-6}$ are as defined below.

Unless defined otherwise, all technical and scientific terms used herein have the same meaning as commonly understood by one of ordinary skill in the art to which this invention belongs.

As used in the specifications and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

As used herein, "heteroatom" refers to non-hydrogen and non-carbon atoms, such as, for example, O, S, and N.

As used herein, "alkyl" refers to a linear, branched or cyclic, saturated or unsaturated hydrocarbon group, which can be unsubstituted or is optionally substituted with one or more substituents. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups.

The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, "alkenyl" means a hydrocarbon moiety that is linear, branched or cyclic and comprises at least one carbon to carbon double bond, which can be unsubstituted or optionally substituted with one or more substituents.

As used herein, "alkynyl" means a hydrocarbon moiety that is linear, branched or cyclic and comprises at least one carbon to carbon triple bond; which can be unsubstituted or optionally substituted with one or more substituents.

As used herein, "aryl" refers to hydrocarbons derived from benzene or a benzene derivative that are unsaturated aromatic carbocyclic groups of from 6 to 100 carbon atoms, or which may or may not be a fused ring system. In some embodiments an aryl comprises from 6 to 50 carbon atoms, in other embodiments from 6 to 25 carbon atoms, and in still other embodiments from 6 to 15 carbon atoms, or from 5 to 8 carbon atoms. The aryls may have a single ring or multiple rings. The term "aryl" as used herein also includes substituted aryls. Examples include, but are not limited to phenyl, naphthyl, xylene, phenylethane, substituted phenyl, substituted naphthyl, substituted xylene, substituted 4-ethylphenyl and the like.

As used herein, "heteroaryl" means a moiety including a substituted or unsubstituted aromatic ring having at least one heteroatom in one or more conjugated aromatic rings. In one embodiment, a heteroaryl comprises from 4 to 8 carbon atoms in addition to the at least one heteroatom. As used herein, "heteroatom" refers to non-carbon and non-hydrogen atoms, such as, for example, O, S, and N. Examples of heteroaryl moieties include pyridyl, furanyl and thienyl.

As used herein, "alkylene" means a divalent alkyl radical, e.g., —$C_fH_{2f}$— wherein f is an integer.

As used herein, "alkenylene" means a divalent alkenyl radical, e.g., —CHCH—.

As used herein, "halogen" or "halo" refers to F, Cl, Br or I. The term "halide" refers to a halogen atom bearing a negative charge.

As used herein, "substituted" means having one or more substituent moieties whose presence does not interfere with the desired reaction or reactivity. Examples of substituents include alkyl, alkenyl, alkynyl, aryl, aryl-halide, heteroaryl, cycloalkyl (non-aromatic ring), Si(alkyl)$_3$, Si(alkoxy)$_3$, halo, alkoxyl, amino, alkylamino, alkenylamino, amide, amidine, hydroxyl, thioether, alkylcarbonyl, alkylcarbonyloxy, arylcarbonyloxy, alkoxycarbonyloxy, aryloxycarbonyloxy, carbonate, alkoxycarbonyl, aminocarbonyl, alkylthiocarbonyl, phosphate, phosphate ester, phosphonato, phosphinato, cyano, acylamino, imino, sulfhydryl, alkylthio, arylthio, thiocarboxylate, dithiocarboxylate, sulfate, sulfato, sulfonate, sulfamoyl, sulfonamide, nitro, nitrile, azido, heterocyclyl, ether, ester, silicon-containing moieties, thioester, or a combination thereof. The substituents may themselves be substituted. For instance, an amino substituent may itself be mono or independently disubstituted by further substituents defined above, such as alkyl, alkenyl, alkynyl, aryl, arylhalide and heteroarylcycloalkyl (non-aromatic ring).

The present application provides catalysts that are useful in the process of catalytic hydrogenation (reduction). The catalytic processes are useful in hydrogenation of, for example, $C_2$-$C_n$ (e.g., n=3-200) substrates possessing one or more moiety that can be hydrogenations, such as ester, lactone, enal, enone and enoate groups, to afford the corresponding reduced moiety, such as the corresponding alcohol, diol, triol or amine products. In some embodiments, hydrogenation of the carbonyl functionality of said ester, lactone, enal, enone and enoate groups proceeds chemoselectively and/or regioselectively. In other embodiments, hydrogenation of the carbonyl functionality of said ester, lactone, enal, enone and enoate groups proceeds stereoselectively.

Thus, the present application further provides a reduction method or process that can be used in place of the main-group hydride reduction to obtain products, such as alcohols, diols, or triols, in a simple, efficient, and "green" fashion. The catalysts of the present application are also useful in the process of catalytic dehydrogenation, which can be a homogeneous dehydrogenation process.

Catalyst Compounds

The processes described herein are carried out in the presence of a catalyst or a pre-catalyst in the form of a transition metal complex of Formulae IV or V

     (IV)

     (V)

wherein M is a transition metal;
each X represents simultaneously or independently a hydrogen or a halogen atom, a $C_1$-$C_5$ alkyl radical, a hydroxyl group, or a $C_1$-$C_7$ alkoxy radical;
Y is CO, NO, carbene, isonitrile, nitrile, phosphite, phosphinite, or a phosphine, such as PMe$_3$, PPh$_3$, PCy$_3$, P(iPr)$_3$;
k is an integer 1 or 2; and PWNN and PWNWP are ligands represented by Formula A

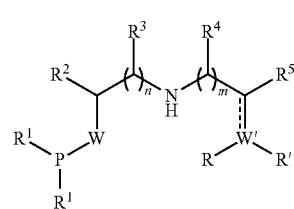

Formula A wherein
each $R^1$, $R^2$, $R^3$, and $R^4$ are each independently H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, or when taken together with the atoms to which they are attached, any two of the $R^2$, $R^3$, $R^4$ groups form an optionally substituted saturated or partially saturated cycloalkyl, or an optionally substituted aryl or heteroaryl;
W is an oxygen atom or an NH group;
W' is an oxygen or a nitrogen atom;
the dashed line is either present and denotes the presence of one bond of a double bond or is absent;
R is absent, H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group;
R' is H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, PR$_2$ or, when taken together with $R^5$ and the atoms to which they are attached forms a substituted or unsubstituted heteroaryl (non-limiting examples of which are pyridyl, furanyl, imidazolyl, pyrazolyl or oxazolyl); and
n and m are each independently an integer 1 or 2
wherein in the PWNN ligand W' is a nitrogen atom and in the PWNWP ligand W' is an oxygen or a nitrogen atom and R' is PR$_2$, and
wherein the metal complex of Formulae IV or V is either neutral or cationic.

In one embodiment, the PWNN ligand has the structure of Formula Ia, Ib, or Ic,

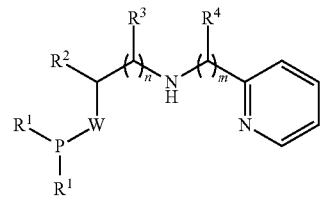

Formula Ia

-continued

Formula Ib
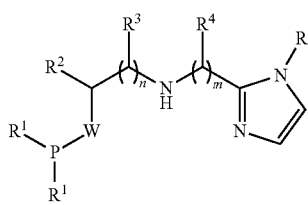

Formula Ic
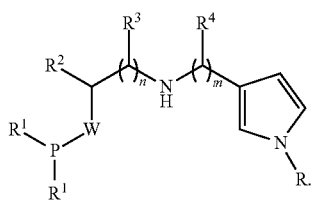

In certain embodiments, the n is 1, or m is 1 or both n and m are 1.

In one example, the transition metal complex comprises a PWNN ligand having the structure of Formula I or Formula II, Formula I
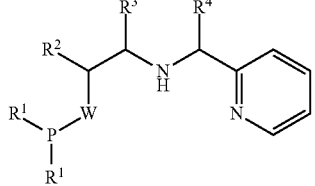

Formula II
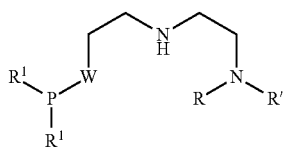

wherein in Formula II, R is not absent.

In an alternative example, the transition metal complex comprises a PWNWP ligand that has the structure of Formula III, Formula III
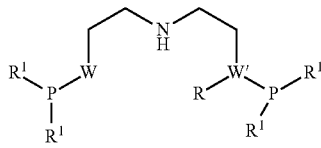

wherein when W' is an oxygen atom R is absent and when W' is a nitrogen atom R is H The PWNN ligand can be obtained using standard procedures that are well known to the person skilled in the relevant art having regard to the current state of the art of chemical synthesis. For example, the PWNN ligand of Formula I can be obtained by condensation of 2-pyridinecarboxaldehyde with ethylenediamine followed by $NaBH_4$ reduction of the intermediate imine and phosphination of the primary amine group with chlorophosphines, $ClP(R_1)_2$. In another example, the PWNN and PWNWP ligands of Formulae II and III, respectively, can be obtained via phosphination of diethylenetriamine or diethanolamine with chlorophosphines.

The transition metal of the metal complex can be a group 7 (manganese group) metal, a group 8 (iron group) metal, group 9 (cobalt group) metal, or group 10 (nickel group) metal.

Preferably, the transition metal is a group 8 metal, such as, for example, osmium or ruthenium.

In accordance with one embodiment, the catalyst or pre-catalyst has the structure of any one of the following formulae:

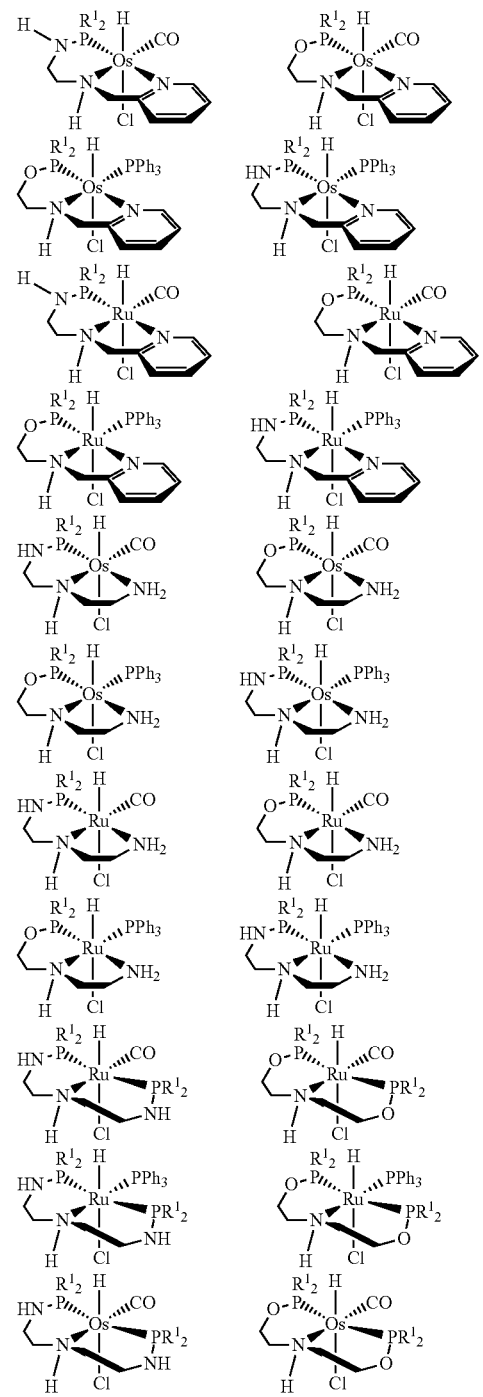

-continued

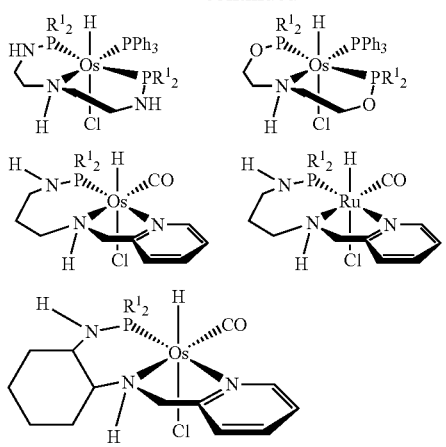

In another embodiment, the complexes of Formulae IV and V can be prepared by reaction of the ligand of Formula A, for examples a ligand of Formulae Ia, Ib, Ic, I, II or III with a metal precursor, such as those well known in the state of the art. Preferably, the metal precursor is a ruthenium or osmium compound, including, for example, the following formulae: $RuCl_2(AsPh_3)_3$, $RuHCl(AsPh_3)_3$, $RuCl_2(PPh_3)_3$, $RuHCl(PPh_3)_3$, $RuCl_2(CO)(PPh_3)_3$, $RuCl_2(CO)(AsPh_3)_3$, $RuHCl(CO)(AsPh_3)_3$, $OsHCl(AsPh_3)_3$, $OsCl_2(AsPh_3)_3$, $OsHCl(PPh_3)_3$, $OsCl_2(PPh_3)_3$, $[RuCl_2(p\text{-cymene})]_2$, $[OsCl_2(p\text{-cymene})]_2$, $RuCl_2(CO)(p\text{-cymene})$, $RuCl_2(PMe_3)(p\text{-cymene})$, $RuCl_2(NHC)(p\text{-cymene})$, $RuCl_2(PCy_3)(p\text{-cymene})$, $RuCl_2(PiPr_3)(p\text{-cymene})$, $OsCl_2(CO)(p\text{-cymene})$, $OsCl_2(NHC)(p\text{-cymene})$, $RuCl_2(CO)(DMF)(PPh_3)_2$, $[IrCl(COD)]_2$, $[IrCl(COE)_2]_2$, $IrHCl_2(PPh_3)_3$, $IrH_2Cl(PPh_3)_3$, $IrHCl_2(AsPh_3)_3$, or $IrH_2Cl(AsPh_3)_3$. The reactions can be conducted in various organic solvents, such as, but not limited to, toluene, xylene, benzene, diglyme, DMF, or DME.

Hydrogenation Process

The present application additionally provides a catalytic hydrogenation process. The catalyst complexes of Formulae IV and V described above, have been shown to have high reactivity in reduction of C=O and C=N bonds. For example, esters, ketones, enals, enones, enoates, plant and seed oils, esters with multiple ester groups and imines can be hydrogenated using the presently described catalytic hydrogenation process.

In one embodiment, there is provided a process for hydrogenation of esters using metal catalysts based on the PWNN or PWNWP ligands of Formula A, such as Formulae Ia, Ib, Ic, I, II or III. The ester substrates are, for example, compounds of the following formulae:

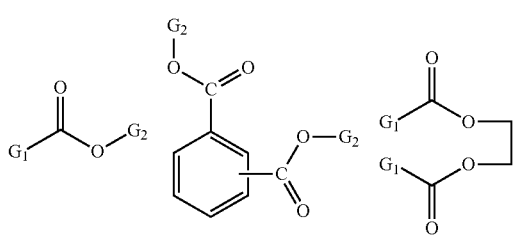

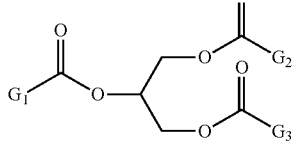

In another embodiment, there is provided a process of hydrogenation of enals, enones, and enolates using metal catalysts based on the PWNN or PWNWP ligands of Formula A, such as Formulae Ia, Ib, Ic, I, II or III. General examples of enal, enone, and enolate substrates are as follows:

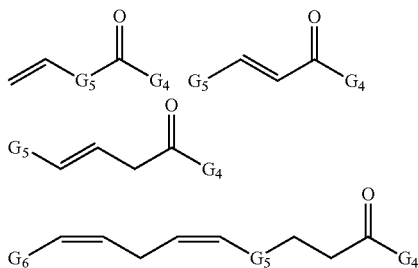

The term "substrate", as used herein and as commonly understood, refers to the reactant that will be converted to a product during a catalytic reaction. Groups $G_1$-$G_6$ simultaneously or independently, represent a linear, branched $C_1$-$C_{40}$ or cyclic $C_3$-$C_{40}$ alkyl, alkenyl or aromatic group, optionally substituted. Also, in certain examples any two of $G_1$-$G_6$, together with the carbon atoms to which they are attached, form a $C_4$-$C_{40}$ saturated or an unsaturated radical, that can contain one or more heteroatom. The substrate of the hydrogenation reaction can be any organic compound containing one, or more than one, carboalkoxy group, C=O, or C=N group. In this respect, natural fats such as olive, canola, corn, peanut, palm and other plant and seed oils are useful substrates that can be reduced using the catalytic hydrogenation process defined herein to give a mixture of alcohols. The present catalytic hydrogenation process can also be used to reduce imines to produce the corresponding amines, and to reduce ketones to the corresponding secondary alcohols.

The catalytic reduction reaction of the present application can proceed, generally, according to a reaction scheme as set out below:

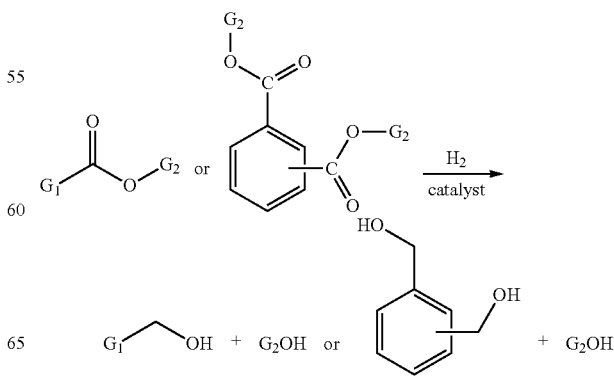

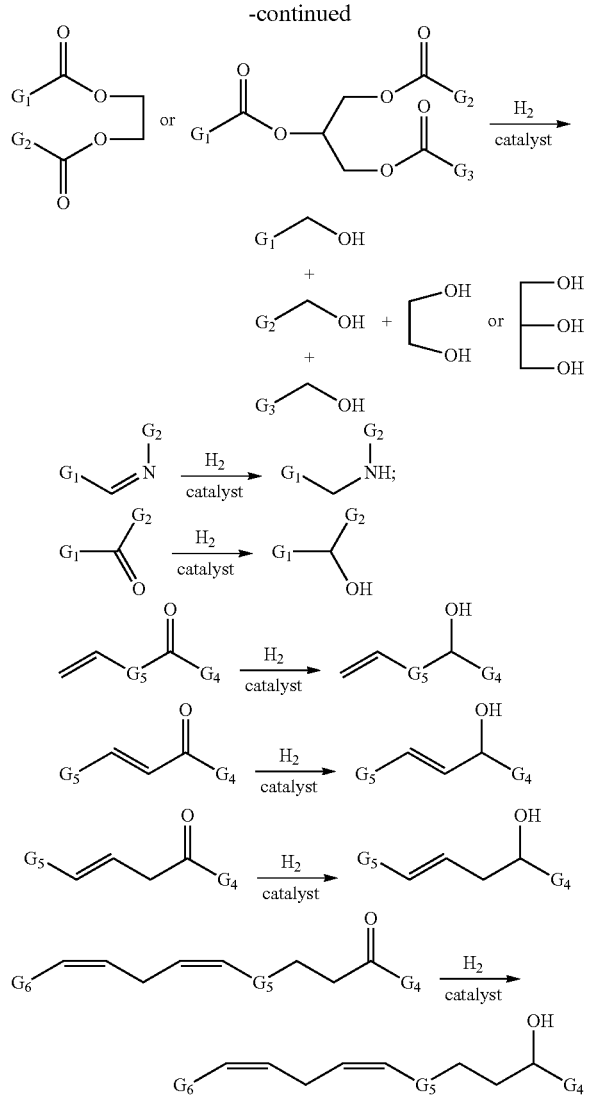

When the substrate is a monoester or a lactone, the products are alcohols or a diol, respectively. The naturally occurring triglycerides, oils and fats can be reduced to glycerol and the corresponding fatty alcohols. Substrates with multiple ester groups, like phthalates, are reduced to diols and polyols. When the substrates are imines or ketones, the products are secondary amines and alcohols, respectively. When the substrates are enones, enals, aor enolates, the products are enols.

According to one embodiment of the invention, the process of catalytic reduction of imines and esters, enals, enones, and enolates, comprises the use of at least one of the metal complexes of Formula IV or V, hydrogen gas at a particular pressure, and, optionally, a base and/or a solvent. The base can be necessary in those cases when the metal catalysts of Formula IV or V contain one or more halogen atoms bonded to the metal. The treatment with base can be done prior to the reduction or in situ by adding base to the reaction mixture during hydrogenation.

The catalysts and pre-catalysts of this invention can be used in a wide range of concentrations, preferably between about 10-1000 ppm, where loadings of about 500 ppm or less are particularly preferred. The preferred amount of the catalyst will depend, as it is known to the person skilled in the art, on the type of substrate, and increasing the catalyst loading can result in faster hydrogenation.

In one embodiment, the temperature at which the hydrogenation is carried out is between about 0° C. and about 150° C., or more preferably in the range between about 20° C. and about 100° C. As would be readily understood by the person skilled in the art, the reaction rate will increase with increase of the reaction temperature. Selection of the appropriate temperature will depend on various factors, including, but not limited to, the overall process performance requirements as determined, for example, by industrially relevant commercial or economic requirements.

The hydrogenation reaction requires a pressure of $H_2$ gas and should be performed in a suitable pressure vessel. As would be readily appreciated by a worked skilled in the art, the surface area of the reactor as well as the hydrogen pressure, can greatly influence the reaction rate. The greater the hydrogen pressure and the surface area of the reactor, the faster is the hydrogenation reaction rate. In certain examples, the catalytic reaction is performed using a hydrogen pressure in range of about 1-200 Bar. Again, the person skilled in the art is well able to adjust the pressure as a function of the catalyst load and of the dilution of the substrate in the solvent. In particular examples, typical hydrogen pressures are in the range of about 5 to 50 bar (or 5 to $50\times10^5$ Pa).

It should be well understood, however, that the catalyst complexes described herein are also useful in catalyzing hydrogenation of substrates including functional groups other than esters and imines, enals, enones, and enolates. The table below provides a non-limiting list of substrate types and products that can be formed from a catalytic hydrogenation reaction using the catalysts of Formula IV or V.

| Hydrogenation Substrate | Product |
| --- | --- |
| Aldehyde | alcohol |
| Ketone | alcohol |
| Ester | alcohol |
| carboxylic acid | alcohol |
| Ketene | alcohol |
| Enol | alcohol |
| Epoxide | alcohol |
| Aldimine | amine |
| Ketimine | amine |
| ketene-imine | amine |
| Nitrile | amine |
| Aziridine | amine |
| Nitro | amine |
| Diazo | amine |
| Isocyanide | amine |
| Enamine | amine |
| Lactone | diol |
| Amide | amine + alcohol |
| Aminoboranes | amine-borane |
| Borazine | amine-borane |
| Olefin | alkane |
| Acetylene | alkane |
| Allene | alkane |

Dehydrogenation Reaction

The present application further provides a process of catalytic dehydrogenation using the catalyst complexes of Formula IV or V. For example, these catalysts or pre-catalysts are suitable for dehydrogenation of $C_n$ (n=2-200) alcohols possessing one or more —$CH_2OH$ groups thereby affording hydrogen gas and the corresponding esters or lactones. The substrates are compounds of the following formulae:

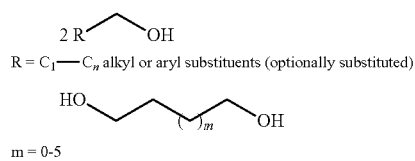

R = C$_1$—C$_n$ alkyl or aryl substituents (optionally substituted)

m = 0-5

In this embodiment, R groups, simultaneously or independently, represent a linear, branched C$_1$-C$_{40}$ or cyclic C$_3$-C$_{40}$ alkyl, alkenyl or aromatic group, optionally substituted. In an alternative embodiment, R is a C$_4$-C$_{40}$ saturated or an unsaturated cyclic radical. Thus, the substrate can be any organic compound containing one, or more than one, hydroxyl (OH) group.

The dehydrogenation process of the present application is generally illustrated below. When the substrate is an alcohol or a diol, the product is an ester or a lactone, respectively.

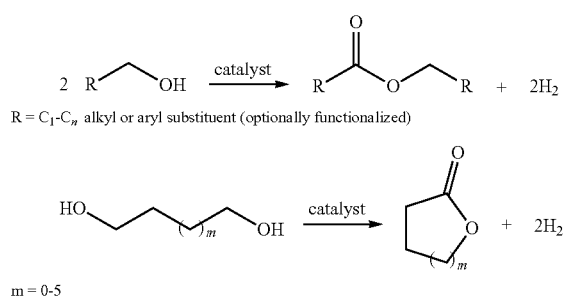

R = C$_1$-C$_n$ alkyl or aryl substituent (optionally functionalized)

m = 0-5

According to one embodiment, the process of catalytic, acceptorless dehydrogenation employs at least one of the metal complexes of Formula IV or V and (optionally) the use of a base and a solvent. The base may be necessary in those cases when the metal catalysts of Formula IV or V contain one or more halogen atoms bonded to the metal. The catalyst can be treated with base prior to mixing with the substrate or in situ, by adding base to the reaction mixture during dehydrogenation. The catalysts and pre-catalysts described herein can be used in a wide range of concentrations, preferably between about 10-1000 ppm, where loadings of about 1000 ppm or less are particularly preferred. The preferred amount of the catalyst will depend, as it is known to the person skilled in the art, on the type of substrate; and increasing the catalyst loading can result in faster dehydrogenation.

The temperature at which the dehydrogenation can be carried out is typically between about 0° C. and about 200° C., more preferably in the range between about 50° C. and about 150° C. As it is well known to the person skilled in the art, the reaction rate will increase with increase of the reaction temperature. The dehydrogenation process can generate a pressure of H$_2$ gas, in which case the reaction is performed in a suitable pressure vessel, optionally equipped with a pressure-release valve.

It should be well understood, that the catalyst complexes described herein are also useful in catalyzing dehydrogenation of substrates including functional groups other than alcohols. The table below provides a non-limiting list of substrates and products that can be formed from a catalytic dehydrogenation reaction using the catalysts of Formula IV or V.

| Substrate | Product[a] |
|---|---|
| alcohols | Ester |
| alcohol | Aldehyde |
| alcohol | Ketone |
| diol | Lactone |
| amine + alcohol | Amide |
| amine + alcohol | substituted amine |
| amine + alcohol | Imine |
| ammonia-borane | aminoboranes |
| ammonia-borane | Borazine |
| amine | Imine |
| amines | Guanidine |
| alcohol + thiol | Thioester |
| thiol | Sulphoxide |
| alcohol + phosphine | acyl phosphine |

[a]H$_2$ is also a byproduct of these reactions. It is either liberated from the reaction as H$_2$ or transferred to an acceptor.

As noted above, a byproduct of the dehydrogenation reactions is H$_2$. Accordingly, the present application further provides a process for producing H$_2$. The process can conveniently make use of readily available substrates in a straightforward catalytic dehydrogenation process under relatively mild conditions to generate H$_2$.

To gain a better understanding of the invention described herein, the following examples are set forth. It should be understood that these examples are for illustrative purposes only. Therefore, they should not limit the scope of this invention in any way.

EXAMPLES

Unless mentioned otherwise, all manipulations were performed under an inert gas (argon or nitrogen) in gloveboxes or using standard Schlenk techniques. NMR spectra were recorded on a Varian Unity Inova 300 MHz spectrometer. All $^{31}$P chemical shifts were measured relative to 85% H$_3$PO$_4$. $^1$H and $^{13}$C chemical shifts were measured relative to the solvent peaks, but are reported relative to TMS. OsO$_4$ and OsCl$_3$.nH$_2$O (54.98% Os) was purchased from Heraeus South Africa. Ru-MACHO, the Milstein's and Firmenich catalysts were purchased from Strem. All other chemicals and anhydrous grade solvents were obtained from Aldrich and Alfa Aesar. All commercial substrates used in the hydrogenation were purified by passing them (neat) through 5 cm×2 cm plug of basic alumina. (NEt$_4$)$_2$OsCl$_6$, OsHCl(CO)(AsPh$_3$)$_3$, and Di(1-adamantyl)chlorophosphine were prepared according to previously reported methods [D. G. Gusev, F. M. Dolgushin, M. Yu. Antipin, *Organometallics* 2001, 20, 1001; D. Spasyuk, S. Smith, D. G. Gusev, *Angew. Chem.* 2012, 51, 2772-2775; A. Köllhofer, H. Plenio, Chem. Eur. J. 2003, 9, 1416-1425; J. R. Goerlich, R. Schmutzler, *Phosphorus. Sulfur. and Silicon.* 1995, 102, 211-215]. Py=2-pyridyl group.

Example 1

Synthesis of H$_2$N(Ch$_2$)$_2$NHCH$_2$Py

All manipulations were carried in air. 2-Picolyl aldehyde (19.0 g, 0.178 mol) in 100 mL of methanol was added during 2 h to a solution of 1,2-ethanediamine (21.3 g, 0.178 mol) in 50 ml of methanol, and the mixture was stirred for 1 h. The resulting solution was treated portion-wise with NaBH$_4$ (17.5 g, 0.461 mol) during 1 h, and the reaction mixture was left to stir for 1 h. After that time, methanol was removed in vacuo and the remaining semisolid was treated with 100 mL of aqueous NaOH (20 wt %) and the product was extracted with 3×50 mL of iPrOH. The combined extract was evaporated under vacuum, and the product was isolated by vacuum distillation (bp132-137° C., 0.1 mmHg) as a colorless liquid (15.3 g, 57%). $^1$H NMR ([D]Chloroform) δ 8.53 (ddd, J=4.9, 1.7, 0.9 Hz, 1H, Py), 7.62 (td, J=7.7, 1.8 Hz, 1H, Py), 7.29 (d, J=7.8 Hz, 1H, Py), 7.22-7.03 (m, 1H, Py), 3.90 (s, 2H, CH$_2$), 2.88-2.75 (m, 2H, CH$_2$), 2.75-2.62 (m, 2H, CH$_2$), 1.49 (br, 3H, NH). $^{13}$C{$^1$H} NMR ([D]Chloroform) δ 160.16 (s, Py), 149.44 (s, Py), 136.48 (s, Py), 122.29 (s, Py), 121.97 (s, Py), 55.32 (s, CH$_2$), 52.54 (s, CH$_2$), 42.07 (s, CH$_2$).

Example 2

Synthesis of (iPr)$_2$PNH(CH$_2$)$_2$NHCH$_2$Py

To a solution of NH$_2$(CH$_2$)$_2$NHCH$_2$Py (2.00 g, 13.2 mmol) and triethylamine (1.6 g, 15.8 mmol) in THF (25 mL) was added chlorodiisopropyl phosphine (96% assay, 2.09 g, 13.2 mmol). The resulting mixture was stirred for two hours and then evaporated to give an oily residue. The product was extracted with hexanes (3×25 mL), filtered through a glass frit and evaporated to give a colorless oil (3.19 g, 90%). $^1$H{$^{31}$P} NMR ([D6]Benzene) δ 8.48 (dd, J=4.8, 2.7 Hz, 1H, Py), 7.14-7.00 (m, 2H, Py), 6.64 (ddd, J=6.7, 4.8, 1.8 Hz, 1H, Py), 3.86 (s, 2H, CH$_2$), 2.99 (q, J=6.1 Hz, 2H, CH$_2$), 2.57 (t, J=5.9 Hz, 2H, CH$_2$), 1.83 (br, 1H, NH), 1.46 (hept, J=7.0 Hz, 2H, CH), 1.19 (br, 1H, NH), 1.04 (d, J=7.1 Hz, 6H, CH$_3$), 1.00 (d, J=6.9 Hz, 6H, CH$_3$). $^{13}$C{$^1$H} NMR ([D6]Benzene) δ 161.27 (s, Py), 149.51 (s, Py), 135.84 (s, Py), 121.95 (s, Py), 121.62 (s, Py), 55.57 (s, CH$_2$), 52.48 (d, J(CP)=6.2 Hz, CH$_2$), 48.87 (d, J(CP)=23.7 Hz, CH$_2$), 26.99 (d, J(CP)=13.2 Hz, CH$_3$), 19.48 (d, J(CP)=20.9 Hz, CH), 17.67 (d, J(CP)=8.3 Hz, CH$_3$). $^{31}$P {$^1$H} NMR ([D6]Benzene) δ 65.58 (s).

Example 3

Synthesis of HO(CH$_2$)$_2$NHCH$_2$Py

All manipulations were carried in air. 2-Picolyl aldehyde (49.3 g, 0.461 mol) in 150 mL of methanol was slowly added to a solution of 2-ethanolamine (28.1 g, 0.461 mol) in 50 ml of methanol, and the mixture was stirred for 1 h. The resulting solution was treated portion-wise with NaBH$_4$ (17.5 g, 0.461 mol) during 1 h, and the reaction mixture was stirred for 1 h. After that time, methanol was removed in vacuo and the remaining semisolid was treated with 100 mL of aqueous NaOH (20 wt %), and the product was extracted with 3×50 mL of iPrOH. The combined extract was evaporated and the product was isolated by distillation (bp 130-132° C., 0.1 mmHg) as a colorless liquid (28.1 g, 40%). $^1$H NMR ([D6]Benzene) δ 8.42 (d, J=4.5 Hz, 1H, Py), 7.06 (td, J=7.6, 1.7 Hz, 1H, Py), 6.94 (d, J=7.7 Hz, 1H, Py), 6.62 (dd, J=7.0, J=5.4 Hz, 1H, Py), 3.77 (s, 2H, CH$_2$), 3.67-3.52 (m, 2H, CH$_2$), 3.13 (br, 2H, OH and NH), 2.71-2.48 (m, 2H, CH$_2$). $^{13}$C{$^1$H} NMR ([D]Chloroform) δ 169.52 (s, Py), 149.76 (s, Py), 136.88 (s, Py), 122.73 (s, Py), 121.42 (s, Py), 61.56 (s, CH$_2$), 55.18 (s, CH$_2$), 51.86 (s, CH$_2$).

Example 4

Synthesis of (iPr)$_2$PO(CH$_2$)$_2$NHCH$_2$Py

To a solution of HO(CH$_2$)$_2$NHCH$_2$Py (2.00 g, 13.2 mmol) and triethylamine (1.60 g, 15.8 mmol) in THF (25 mL) was added chlorodiisopropyl phosphine (96% assay, 2.09 g, 13.2 mmol). The resulting mixture was stirred for two hours then evaporated to give an oily residue. The product was extracted with hexanes (3×25 mL), filtered through a glass frit and evaporated to give a colorless oil (3.31 g, 94%). $^1$H NMR ([D6]Benzene) δ 8.62-8.30 (m, 1H, Py), 7.13-7.06 (m, 2H, Py), 6.73-6.52 (m, 1H, Py), 3.89 (s, 2H, CH$_2$), 3.87-3.73 (m, 2H, CH$_2$), 2.72 (t, J=5.5 Hz, 2H, CH$_2$), 2.05 (br, 1H), 1.71-1.49 (m, 2H, CH), 1.12 (dd, J=10.2, 7.0 Hz, 6H, CH$_3$), 1.00 (dd, J=15.3, 7.2 Hz, 6H, CH$_3$). $^{13}$C{$^1$H} NMR ([D6]Benzene) δ 161.56 (s, Py), 149.83 (s, Py), 136.17 (s, Py), 122.16 (s, Py), 121.93 (s, Py), 72.68 (d, J(CP)=19.2 Hz, CH$_2$), 55.97 (s, CH$_2$), 51.25 (d, J(CP)=6.9 Hz, CH$_2$), 28.81 (d, J(CP)=17.8 Hz, CH), 18.51 (d, J(CP)=20.8 Hz, CH$_3$), 17.53 (d, J(CP)=8.6 Hz, CH$_3$).

Example 5

Synthesis of (tBu)$_2$PNH(CH$_2$)$_2$NHCH$_2$Py tBu$_2$PCl (96% assay 12.42 g, 66 mmol) was added to a solution of NH$_2$(CH$_2$)$_2$NHCH$_2$Py (10.0 g, 66.0 mmol) and triethylamine (8 g, 79 mmol) in THF (100 mL). The resulting mixture was stirred for 16 hours, then filtered to remove precipitated triethylammonium chloride; the filtrate was evaporated under vacuum. The solid left after evaporation was re-dissolved in a hexane/Et$_2$O solvent mixture (3:1, 40 mL), then filtered through a 1 cm layer of activated basic alumina on a glass frit. Further 3×6 mL of the hexane/Et$_2$O mixture was used to wash the alumina. The filtrate was evaporated and dried under vacuum to give a white solid (18.2 g, 93%). $^1$H NMR ([d$_6$]Benzene) δ 8.48 (d, J=4.9 Hz, 1H, Py), 7.20-6.97 (m, 2H, Py), 6.64 (ddd, J=6.5, 4.9, 1.7 Hz, 1H, Py), 3.87 (s, 2H, CH$_2$), 3.05 (m, 2H, CH$_2$), 2.62 (t, J=5.9 Hz, 2H, CH$_2$), 1.88 (br, 1H, NH), 1.49 (br, 1H, NH), 1.08 (d, J(HP)=11.1 Hz, 18H, CH$_3$). $^{13}$C{$^1$H} NMR ([d$_6$]Benzene) δ 161.27 (s, Py), 149.54 (s, Py), 135.84 (s, Py), 121.97 (s, Py), 121.63 (s, Py), 55.54 (s, J(CP)=3.0 Hz, CH$_2$), 52.33 (d, J(CP)=7.2 Hz, CH$_2$), 50.66 (d, J(CP)=29.0 Hz, CH$_2$), 34.12 (d, J(CP)=21.6 Hz, C{tBu}), 28.59 (d, J(CP)=15.3 Hz, CH$_3$). $^{31}$P {$^1$H} NMR ([d$_6$]Benzene) δ 79.36 (s).

Example 6

Synthesis of (Ad)$_2$PNH(CH$_2$)$_2$NHCH$_2$Py

Ligand was prepared similar to the procedure reported for (iPr)$_2$PNH(CH$_2$)$_2$NHCH$_2$Py ligand except toluene (3×20 mL) was used for ligand extraction. The ligand was obtained as a viscous colorless oil. Yield 87%. $^1$H NMR ([d$_6$] Benzene) δ 8.49 (dt, J=4.8, 1.3 Hz, 1H, Py), 7.22-6.98 (m, 1H, Py), 6.89 (d, J=7.6 Hz, 1H, Py), 6.73-6.51 (m, 1H, Py), 3.92 (s, 2H, CH$_2$), 3.10 (m, 2H, CH$_2$), 2.70 (t, J=5.8 Hz, 2H, CH$_2$), 2.22-1.61 (m, 32H, Ad+NH). $^{13}$C([d$_6$]Benzene) δ 145.58 (s, Py), 131.96 (s, Py), 122.50 (s, Py), 118.19 (s, Py), 117.79 (s, Py), 51.50 (s, CH$_2$), 48.32 (d, J=7.1 Hz, CH$_2$), 47.10 (d, J=29.5 Hz, CH$_2$), 36.14 (d, J=12.7 Hz, Ad), 34.81 (d, J=21.5 Hz, Ad), 33.70 (s, Ad), 25.17 (d, J=8.2 Hz, Ad). $^{31}$P{$^1$H} NMR ([d$_6$]Benzene) δ 77.17 (s).

Example 7

Synthesis of [OsCl$_2$(p-cymene)]$_2$

This preparation was based on a reported procedure (R. Castarlenas, M. A. Esteruelas, E. Oñate, *Organometallics* 2005, 24, 4343-4346, incorporated by reference herein in its entirety): all manipulations were performed under argon.

α-Terpinene (60 mL, ≥89%, Aldrich W355801) in 240 mL of anhydrous 2-propanol (Aldrich 278475) was added to 20 g of Os(III) chloride (54.98% Os, 57.8 mmol) in a 0.5 L flask to give a dark solution upon stirring. The flask was fitted with a condenser, and the reaction mixture was refluxed while stirring for 16 h. After cooling to room temperature, the flask was kept in a freezer at −15° C. for 1 h, then the product was filtered, washed with 4×50 mL of 2-propanol, and dried under vacuum for 3 h. Yield: 20.77 g (90.9%) of an orange powdery solid.

In one synthesis, performed on a 3 g scale, the product was recrystallized from 120 mL of hot 2-propanol. This would not be practical in a large-scale preparation of [$OsCl_2$(p-cymene)]$_2$, given that the osmium dimer has a limited solubility in 2-propanol (and in most organic solvents except dichloromethane). However, [$OsCl_2$(p-cymene)]$_2$ did dissolve in ethanol when stirred with $PyCH_2NHC_2H_4NHPtBu_2$ and lithium in preparation of OsHCl(CO)($PyCH_2NHC_2H_4NHPtBu_2$) (vide infra), and this solution could be filtered, as necessary.

Example 8

Synthesis of OsHCl(CO)[(iPr)$_2$PNH(CH$_2$)$_2$NHCH$_2$Py] (1a)

A flask containing a mixture of OsHCl(CO)(AsPh$_3$)$_3$ (1.74 g, 1.49 mmol) and (iPr)$_2$PNH(CH$_2$)$_2$NHCH$_2$Py (400 mg, 1.49 mmol) in 15 mL of m-xylene was placed in a preheated to 150° C. oil bath and stirred for 1 h, affording a dark-red suspension. After cooling to room temperature, the mixture was placed in a freezer at −13° C. for 2 h. The precipitated product was filtered off, washed with diethyl ether (3×2 mL), and dried under vacuum for 1 h to give a brown-grey solid. Yield: 660 mg (85%). $^1$H{$^{31}$P} NMR (([d$_2$]DCM) δ 8.98 (d, J=5.6 Hz, 1H, Py), 7.71 (t, J=7.7 Hz, 1H, Py), 7.36 (d, J=7.8 Hz, 1H, Py), 7.25 (t, J=6.2 Hz, 1H, Py), 4.49 (d, J=10.8 Hz, 1H, CH$_2$), 4.05-3.76 (m, 2H, CH$_2$), 3.48-2.99 (m, 3H), 2.72 (dd, J=20.2, 10.3 Hz, 1H), 2.39 (hept, J=7.2 Hz, 1H, CH), 1.93 (hept, J=6.9 Hz, 1H, CH), 1.83-1.68 (br, 2H), 1.31 (dd, J=7.2 Hz, 3H, CH$_3$), 1.26 (d, J=7.1 Hz, 3H, CH$_3$), 1.09 (t, J=6.4 Hz, 6H, CH$_3$), −16.40 (s, 1H, OsH). $^{13}$C{$^1$H} NMR ([d$_2$]DCM) δ 187.76 (d, J=12.0 Hz, CO), 157.39 (s, Py), 153.39 (s, Py), 136.62 (s, Py), 125.21 (s, Py), 121.31 (s, Py), 62.98 (s, CH$_2$), 57.84 (s, CH$_2$), 44.99 (d, J=3.4 Hz, CH$_2$), 33.33 (d, J=29.9 Hz, CH), 31.32 (d, J=46.0 Hz, CH), 19.08 (d, J=2.2 Hz, CH$_3$), 18.79 (d, J=13.2 Hz, CH$_3$), 18.03 (s, CH$_3$). $^{31}$P {$^1$H} (d$_2$]DCM) δ 72.91 (s).

Example 9

Synthesis of OsHCl(CO)[(tBu)$_2$PNH(CH$_2$)$_2$NHCH$_2$Py] (1b)

Method 1. Anhydrous ethanol (100 mL) was poured into a 300 mL flask equipped with a magnetic stir bar and containing PyCH$_2$NHC$_2$H$_4$NHPtBu$_2$ (5.6 g, 18.96 mmol) and [OsCl$_2$(p-cymene)]$_2$ (7.2 g, 9.11 mmol). Stirring this mixture gave a dark brown solution. Then 136 mg (19.59 mmol) of lithium was added and stirring continued until all lithium was dissolved. The resulting dark-red solution was filtered through a layer of Celite™ (3 g) in a 60 mL fitted funnel, and the filter material was washed with 4×10 mL of anhydrous ethanol. The filtered solution was poured into a 300 mL steel autoclave equipped with a magnetic stir bar, and more ethanol was used to bring the total solvent volume to 150 mL. The autoclave was closed, tightened, and placed into an oil bath preheated to 170° C. on a hotplate stirrer. This temperature was maintained for 3.5 h while stirring at 600 rpm. During this time, pressure was raised to 350 psi. Then, the autoclave was removed from the oil bath, and it was transferred into a cold-water bath. After 1 h, the autoclave was vented, opened in air, and the crystalline product was isolated by vacuum filtration. The autoclave and the filtered solid were liberally washed with denatured ethanol under air, and the product was dried under vacuum of an oil pump (0.01 mmHg). Yield: 7.75 g (77.5%).

Method 2. A flask containing a mixture of OsHCl(CO)(AsPh$_3$)$_3$ (3.48 g, 2.98 mmol) and PyCH$_2$NH(CH$_2$)$_2$NP(tBu)$_2$ (880 mg, 2.48 mmol) in 15 mL of m-xylene was placed in an oil bath preheated to 140° C. and stirred for 2 h, affording a brown suspension. After cooling to room temperature, the mixture was placed in a freezer at −15° C. for 2 h. Precipitated product was filtered off, washed with diethyl ether (3×2 mL), and dried under vacuum for 1 h to give a lemon-yellow microcrystalline solid. Yield: 1.51 g (92%). $^1$H NMR ([d$_2$]DCM) δ 8.99 (d, J=5.3 Hz, 1H, Py), 7.70 (t, J=7.7 Hz, 1H, Py), 7.34 (d, J=7.7 Hz, 1H, Py), 7.25 (t, J=6.5 Hz, 1H, Py), 4.61-4.31 (m, 1H, CH$_2$), 4.08-3.79 (m, 2H, CH$_2$), 3.47-3.12 (m, 3H, CH$_2$+NH), 2.77 (dd, J=18.9, 9.4 Hz, 1H, CH$_2$), 2.04 (br, 1H, NH), 1.39 (d, J=13.1 Hz, 9H, CH$_3$), 1.29 (d, J=12.9 Hz, 9H, CH$_3$), −16.83 (d, J(HP)=19.2 Hz, 1H, OsH).). $^{13}$C{$^1$H} NMR ([d$_2$]DCM) δ 180.35 (d, J(CP)=10.3 Hz, CO), 157.43 (s, Py), 153.44 (s, Py), 136.58 (s, Py), 125.31 (s, Py), 121.17 (s, Py), 62.98 (s, CH$_2$), 57.22 (s, CH$_2$), 46.30 (d, J(CP)=3.7 Hz, CH$_2$), 43.79 (d, J(CP)=22.0 Hz, CH$_2$), 39.72 (d, J(CP)=39.2 Hz, C{tBu}), 30.10 (d, J(CP)=4.6 Hz, CH$_3$), 29.71 (d, J(CP)=2.4 Hz, CH$_3$). $^{31}$P {$^1$H} NMR ([d$_2$]DCM) δ 83.63 (s). Anal. Calcd for C$_{17}$H$_{31}$ClN$_3$OOsP: C, 37.12; H, 5.68; N, 7.64. Found: C, 37.20; H, 5.56; N, 7.42.

Example 10

Synthesis of OsHCl(CO)[(Ad)$_2$PNH(CH$_2$)$_2$NHCH$_2$Py] (1c)

A flask containing a mixture of OsHCl(CO)(AsPh$_3$)$_3$ (1.036 g, 0.887 mmol) and PyCH$_2$NH(CH$_2$)$_2$NP(Ad)$_2$ (400 mg, 0.887 mmol) in 15 mL of m-xylene was placed in an oil bath preheated to 150° C. and stirred for 2 h, affording a dark-brown suspension. After cooling to room temperature, the mixture was placed in a freezer at −15° C. for 2 h. The precipitated product was filtered off, washed with diethyl ether (3×2 mL), and dried under vacuum for 2 h to give a yellow solid. $^1$H NMR ([d$_2$]DCM) δ 8.98 (d, J=2.7 Hz, 1H, Py), 7.68 (t, J=7.5 Hz, 1H, Py), 7.30 (d, J=7.5 Hz, 1H, Py), 7.24 (t, J=6.4 Hz, 1H, Py), 4.45 (dd, J=13.7, 2.3 Hz, 1H, CH$_2$), 4.15-3.74 (m, 2H, CH$_2$+NH), 3.53-3.06 (m, 3H), 2.72 (dd, J=19.5, 9.9 Hz, 1H, CH$_2$), 2.57-1.34 (m, 30H, Ad), −17.01 (d, J(HP)=18.8 Hz, 1H, OsH). $^{13}$C{$^1$H} NMR ([d$_2$]DCM) δ 188.02 (d, J(CP)=11.7 Hz, CO), 157.52 (s, Py), 153.36 (s, Py), 136.44 (s, Py), 125.24 (s, Py), 121.12 (s, Py), 62.86 (s, CH$_2$), 57.24 (s, CH$_2$), 47.66 (d, J(CP)=20.9 Hz, CH$_2$), 46.48 (s, Ad), 43.76 (d, J(CP)=37.3 Hz, Ad), 40.20 (s, Ad), 39.79 (s, Ad), 37.63 (d, J(CP)=14.3 Hz, Ad), 29.77 (d, J(CP)=8.66 Hz, Ad), 29.66 (d, J(CP)=8.33 Hz, Ad). $^{31}$P{$^1$H} NMR ([d$_2$]DCM) δ 81.55 (s). Anal. Calcd for C$_{29}$H$_{42}$N$_3$POClOs: C, 49.31; H, 6.04; N, 5.96. Found: C, 48.20; H, 6.04; N, 5.74.

Example 11

Synthesis of OsHCl(CO)[(iPr)$_2$PO(CH$_2$)$_2$NHCH$_2$Py] (3)

A flask containing a mixture of OsHCl(CO)(AsPh$_3$)$_3$ (1.74 g, 1.49 mmol) and (iPr)$_2$PO(CH$_2$)$_2$NHCH$_2$Py (400 mg, 1.49 mmol) in 23 mL of m-xylene was placed in a preheated to 150° C. oil bath and stirred for 1 h, affording a dark-red suspension. After cooling to room temperature, the mixture was placed in a freezer at −14° C. for 2 h. The precipitated product was filtered off, washed with diethyl ether (3×2 mL), and dried under vacuum for 1 h to give a brown-grey solid. Yield: 530 mg (68%). $^1$H NMR ([d$_2$]DCM) δ 8.94 (d, J=5.4 Hz, 1H, Py), 7.72 (td, J=7.7, 1.1 Hz, 1H, Py), 7.37 (d, J=7.8 Hz, 2H, Py), 7.32-7.22 (m, 1H, Py), 4.54 (dd, J=13.5, 2.9 Hz, 1H, CH$_2$), 4.13-3.72 (m, 4H), 3.37 (dt, J=12.7, J(HP)=3.7 Hz, 1H, CH$_2$), 2.87 (dd, J=21.6, 10.8 Hz, 1H, CH$_2$), 2.77-2.52 (m, 1H, CH), 2.26-2.04 (m, 1H, CH), 1.32 (dd, J=15.7, 7.4 Hz, 3H, CH$_3$), 1.23 (dd, J=13.7, 7.2 Hz, 3H, CH$_3$), 1.09 (dd, J=11.9, J(HH)=3.9 Hz, 3H, CH$_3$), 1.02 (dd, J=14.5, J(HH)=4.3 Hz, 3H, CH$_3$), −16.08 (d, J=20.4 Hz, 1H, OsH). $^{13}$C{$^1$H} NMR ([d$_2$]DCM) δ 187.94 (d, J=10.0 Hz, CO), 157.14 (s, Py), 153.31 (s, Py), 136.96 (s, Py), 125.28 (d, J=1.8 Hz, Py), 121.48 (d, J=2.1 Hz, Py), 66.92 (s, CH$_2$), 62.80 (s, CH$_2$), 56.13 (s, CH$_2$), 33.28 (d, J=29.1 Hz, CH), 32.40 (d, J=46.2 Hz, CH), 18.82 (s, CH$_3$), 18.27 (d, J=3.0 Hz, CH$_3$), 18.15 (d, J=5.8 Hz, CH$_3$), 17.16 (s, CH$_3$). $^{31}$P{$^1$H} NMR ([d$_2$]DCM) δ 136.35 (s).

Example 12

Synthesis of RuHCl(CO)[(tBu)$_2$PNH(CH$_2$)$_2$NHCH$_2$Py] (4)

A flask containing a mixture of RuHCl(CO)(AsPh$_3$)$_3$ (662 g, 0.677 mmol) and PyCH$_2$NH(CH$_2$)$_2$NP(tBu)$_2$ (200 mg, 0.677 mmol) in 10 mL of m-xylene was placed in an oil bath preheated to 140° C. and stirred for 1 h, affording a dark-red suspension. After cooling to room temperature, the mixture was placed in a freezer at −13° C. for 2 h. Precipitated product was filtered off, washed with diethyl ether (3×3 mL), and dried under vacuum for 1 h to give a brown-grey solid. Yield: 271 mg (87%). $^1$H NMR (399 MHz, [d$_2$]DCM) δ 9.05-8.84 (m, 1H, Py), 7.70 (td, J(HH)=7.7, 1.5 Hz, 1H, Py), 7.41-7.09 (m, 2H, Py), 4.25 (dd, J(HH)=14.0, 3.0 Hz, 1H, CH$_2$), 4.00 (dd, J=25.1, 11.4 Hz, 1H, CH$_2$), 3.93 (br, 1H, NH), 3.46-3.12 (m, 3H), 2.67 (m, 1H, CH$_2$), 2.07-1.87 (br, 1H, NHP), 1.39 (d, J(HP)=13.3 Hz, 9H, CH$_3$), 1.28 (d, J(HP)=13.1 Hz, 9H, CH$_3$), −15.11 (d, J(HP)=26.5 Hz, 1H). $^{13}$C{$^1$H} NMR (100 MHz, [d$_2$]DCM) δ 207.67 (dd, J(CP)=18.5 Hz, CO), 157.33 (s, Py), 153.26 (s, Py), 136.96 (s, Py), 124.56 (d, J(CP)=1.9 Hz, Py), 121.23 (d, J(CP)=2.1 Hz, Py), 61.66 (d, J(CP)=1.9 Hz, CH$_2$), 56.30 (s, CH$_2$), 45.35 (d, J(CP)=5.0 Hz, CH$_2$), 42.35 (d, J(CP)=15.7 Hz, C$^{tBu}$), 38.47 (d, J(CP)=33.7 Hz, C$^{tBu}$), 29.87 (d, J(CP)=5.2 Hz, CH$_3$), 29.63 (d, J(CP)=4.0 Hz, CH$_3$). $^{31}$P{$^1$H} NMR ([d$_2$]DCM) δ 12.16 (s). Anal. Calcd for C$_{17}$H$_{31}$ClN$_3$OPRu: C, 44.30; H, 6.78; Cl, 7.69; N, 9.12. Found: C, 43.76; H, 6.58; N, 8.63.

Example 13

Synthesis of OsH$_2$(CO)[(tBu)$_2$PNH(CH$_2$)$_2$NHCH$_2$Py] (5)

A 75 mL high pressure vessel was charged with OsHCl(CO)[(tBu)$_2$PNH(CH$_2$)$_2$NHCH$_2$Py] complex (200 mg, 0.363) and tBuOK (45 mg, 0.399) in 10 mL of THF. The resulting dark red mixture was pressurized with 10 atm of H$_2$ gas and left to stir at room temperature for 2 h. After that time, the reactor was depressurized and taken into a glove box. The resulting brown solution was filtered through a glass frit and THF was reduced in vacuo by 50%. The filtrate was then mixed with 6 mL of hexanes and the product was left to crystallize in a freezer. The OsH$_2$(CO)[(tBu)$_2$PNH(CH$_2$)$_2$NHCH$_2$Py] complex was isolated as a yellow solid by filtration and subsequently dried (for 10 min) under reduced pressure. Yield 112 mg (60%). The complex crystallized as a mixture two fac and mer isomers having limited stability in solution of THF and in solid state. The complex undergoes slow decomposition to OsH(CO)[(tBu)$_2$PNH(CH$_2$)$_2$NCH$_2$Py] complex and hydrogen gas. $^1$H NMR ([d$_8$]THF) δ major isomer (mer) 9.25 (d, J=5.0 1H, Py), 7.49 (t, J=7.4 Hz, 1H, Py), 7.23 (d, J=7.4 Hz, 1H, Py), 6.95 (t, J=5.8 Hz, 1H, Py), 5.15 (br, 1H, NH), 4.38 (dd, J=13.4, J=2.5 Hz, 1H, CH$_2$), 3.80-3.40 (m, 1H, overlaps with [d$_8$]THF), 3.44-3.10 (m, 2H), 3.10-2.84 (m, 2H), 2.75-2.40 (m, 3H), 1.35 (d, J=12.3 Hz, 18H, CH$_3$), −4.45 (dd, J=14.2, 6.5 Hz, 1H, OsH), −4.90 (dd, J(HP)=13.4, J(HH)=6.6 Hz, 1H, OsH), minor isomer (fac) −4.56 (d, J(HH)=6.1 Hz, 1H), −14.32 (dd, J(PH)=17.2, J(HH)=6.7 Hz, 1H). $^{31}$P{$^1$H} NMR ([d$_8$]THF) δ major isomer 101.53 (s), minor isomer 86.95 (s). IR (Nujol): vCO=1867 (s).

Without being bound by theory, Complex (5) is proposed as a potential pre-catalyst or intermediate complex for the hydrogenation of substrates.

Example 14

Crystal Structure Determination of Complexes (1b)-(1c)

Single crystals of complexes 1b and 1c were grown by slow diffusion of hexanes into saturated solutions in dichloromethane. Data for complex 1b was collected on a Bruker Microstar generator equipped with Helios optics, a Kappa Nonius goniometer, and a Platinum-135 detector. Data for complex 1c was collected on a Bruker APEX II QUAZAR equipped with the IµS™ X-ray Source generator, a Kappa Nonius goniometer and a Platinum135 detector. Cell refinement and data reduction were done using SAINT [SAINT (1999) Release 6.06; Integration Software for Single Crystal Data.Bruker AXS Inc., Madison, Wis., USA]. An empirical absorption correction, based on the multiple measurements of equivalent reflections, was applied using the program SADABS [Sheldrick, G. M. (1999). SADABS, Bruker Area Detector Absorption Corrections. Bruker AXS Inc., Madison, Wis., USA]. The space group was confirmed by XPREP routine [XPREP (1997) Release 5.10; X-ray data Preparation and Reciprocal space Exploration Program.Bruker AXS Inc., Madison, Wis., USA] of SHELXTL [SHELXTL (1997) Release 5.10; The Complete Software Package for Single Crystal Structure Determination. Bruker AXS Inc., Madison, Wis., USA]. The structures were solved by direct-methods and refined by full-matrix least squares and difference Fourier techniques with SHELX-2013 [(Sheldrick, G. M. (1997). SHELXS97, Program for the Solution of Crystal Structures. Univ. of Gottingen, Germany; Sheldrick, G. M. (1997). SHELXL97, Program for the Refinement of Crystal Structures. University of Gottingen, Germany] as a part of LinXTL tool box [LinXTL is a local program and was obtained free of charge from http://sourceforge.net/projects/linxtl/]. All non-hydrogen atoms were refined with anisotropic displacement parameters. Hydrogen atoms were set in calculated positions and refined as riding atoms with a common thermal parameter, except those of the NH, OH moieties and hydrides, which were positioned from residual peaks in the difference Fourier map. All publication materials (cif files validation and ORTEP drawings) were prepared using LinXTL and Platon programs [A. L. Spek, *Acta Cryst.* 2009, D65, 148-155]. See FIG. 3, and Tables 1-2.

TABLE 1

Crystal Data Collection and Refinement Parameters for Complex 1b and 1c.

| | 1b | 1c |
|---|---|---|
| chemical formula | $C_{17}H_{31}ClN_3OOsP$ | $C_{29}H_{43}ClN_3OOsP$ |
| crystal colour | Yellow | Yellow |
| Fw; F(000) | 550.07; 1080 | 706.28; 2832 |
| T (K) | 150 | 100 |
| wavelength (Å) | 1.54178 | 1.54178 |
| space group | P21/c | C2/c |
| a (Å) | 12.8403(4) | 29.5260(3) |
| b (Å) | 10.7117(3) | 13.6981(2) |
| c (Å) | 15.9847(5) | 13.5978(2) |
| α (deg) | 90 | 90 |
| β (deg) | 110.275(1) | 90.42 |
| γ (deg) | 90 | 90 |
| Z | 4 | 8 |
| V (Å$^3$) | 2062.3(1) | 5499.5(1) |
| $\rho_{calcd}$ (g · cm$^{-3}$) | 1.772 | 1.706 |
| μ (mm$^{-1}$) | 13.672 | 10.412 |
| θ range (deg); completeness | 3.670-70.056; 0.988 | 2.993-71.248; 0.989 |
| collected reflections; $R_\sigma$ | 66993; 0.0201 | 35741; 0.0200 |
| unique reflections; $R_{int}$ | 66993; 0.0622 | 35741; 0.0339 |
| R1$^a$; wR2$^b$ [I > 2σ(I)] | 0.0426; 0.1371 | 0.0197; 0.0503 |
| R1; wR2 [all data] | 0.0435; 0.1374 | 0.0198; 0.0503 |
| GOF | 1.174 | 1.181 |
| largest diff peak and hole | 3.542 and −1.428 | 0.716 and −0.584 |

$^a R_1 = \Sigma(||F_o| - |F_c||)/\Sigma|F_o|^b wR_2 = \{\Sigma[w(F_o^2 - F_c^2)^2]/\Sigma[w(F_o^2)^2]\}^{1/2}$

TABLE 2

Selected Bond Distances (Å) and Angles (deg) for Complexes 1b and 1c.

| 1b | | 1c | |
|---|---|---|---|
| C17—Os1 | 1.85(1) | C29—Os1 | 1.843(3) |
| Cl1—Os1 | 2.531(2) | Cl1—Os1 | 2.5409(5) |
| N1—Os1 | 2.191(8) | N1—Os1 | 2.187(2) |
| N2—Os1 | 2.133(8) | N2—Os1 | 2.127(2) |

TABLE 2-continued

Selected Bond Distances (Å) and Angles (deg) for Complexes 1b and 1c.

| 1b | | 1c | |
|---|---|---|---|
| Os1—P1 | 2.311(3) | Os1—P1 | 2.2943(6) |
| C17—Os1—N1 | 172.27(9) | C29—Os1—N1 | 172.27(9) |
| N2—Os1—N1 | 76.2(3) | N2—Os1—N1 | 75.49(8) |
| C17—Os1—P1 | 92.1(4) | C29—Os1—P1 | 91.97(8) |
| N1—Os1—P1 | 95.75(6) | N1—Os1—P1 | 95.75(6) |
| C17—Os1—N2 | 95.4(4) | C29—Os1—N2 | 93.78(7) |

Example 15

Typical Procedure for Hydrogenation of Esters Using Complexes (1a), and (3)

A solution of catalyst 1 (5.2 mg/mL) and a base (0.2 mmol) in THF was mixed with 0.02 mol of the ester substrate in 6 mL of THF. The mixture was then transferred into a 75 mL stainless-steel reactor (Parr 4740) equipped with a magnetic stir bar. The reactor was purged by two cycles of pressurization/venting with H$_2$ (150 psi, 10 Bar), pressurized with H$_2$ (725 psi, 50 Bar), and was disconnected from the H$_2$ source. The hydrogenation was conducted at 40-100° C. At the end of the required reaction time, the reactor was placed into a cold-water bath and depressurized after cooling to the ambient temperature.

Table 3, below, summarizes results obtained using complexes (1a) and (3).

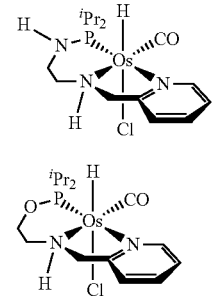

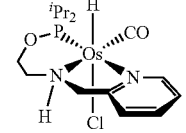

TABLE 3

Hydrogenation of esters, ketones, imines catalyzed by complexes 1a, 3$^a$.

| Entry | Substrate | Cat | Substrate/Catalyst Ratio | t, h | Solvent | Base, mol % | T, ° C. | Conv. (%) |
|---|---|---|---|---|---|---|---|---|
| 1 | Methyl benzoate | 1a | 2000 | 1 | THF | tBuOK, 1 | 100 | 80 |
| 2 | Methyl benzoate | 1a | 2000 | 3 | THF | MeOK, 5 | 40 | 80 |
| 3 | Methyl benzoate | 3 | 2000 | 1 | THF | tBuOK, 1 | 100 | 88 |
| 4 | Methyl hexanoate | 3 | 2000 | 3 | THF | KOMe, 5 | 40 | 22$^b$ |
| 5 | Methyl hexanoate | 1a | 2000 | 3 | THF | KOMe, 5 | 40 | 57$^b$ |
| 6 | Methyl 3-nonenoate | 1a | 4000 | 5 | THF | tBuOK, 1 | 100 | 65 |
| 7 | Methyl 3-nonenoate | 1a | 2000 | 2 | THF | tBuOK, 1 | 100 | 100$^c$ |
| 8 | Methyl 10-undecenoate | 1a | 1000 | 1 | THF | tBuOK, 5 | 100 | 85 |
| 9 | Methyl 10-undecenoate | 1a | 2000 | 2.5 | THF | tBuOK, 1 | 100 | 96$^d$ |
| 10 | Ethyl 10-undecenoate | 1a | 2000 | 2.5 | THF | EtONa, 5 | 80 | 87$^e$ |
| 11 | Ethyl 10-undecenoate | 1a | 2000 | 1 | THF | EtONa, 5 | 100 | 76$^f$ |
| 12 | Methyl linoleate | 1a | 1000 | 4 | THF | tBuOk, 2 | 100 | 100$^g$ |
| 13 | Ethyl chrysanthemate | 1a | 2000 | 22 | THF | tBuOk, 1 | 100 | 100 |
| 14 | Ethyl chrysanthemate | 1a | 2000 | 20 | THF | tBuOk, 1 | 100 | 96$^b$ |
| 15 | Methyl oleate | 1a | 1000 | 4 | THF | tBuOk, 1 | 100 | 100 |

TABLE 3-continued

Hydrogenation of esters, ketones, imines catalyzed by complexes 1a, 3[a].

| Entry | Substrate | Cat | Substrate/Catalyst Ratio | t, h | Solvent | Base, mol % | T, °C. | Conv. (%) |
|---|---|---|---|---|---|---|---|---|
| 16 | Methyl oleate | 3 | 1000 | 4 | THF | tBuOk, 2 | 100 | 12 |
| 17 | Coconut Oil | 1a | 750 | 14 | THF | tBuOK, 3 | 100 | 100 |

[a]reactions were performed using 20 mmol of the substrates in THF at 100° C. and 50 Bar of $H_2$ pressure in a 75 mL autoclave.
[b]reaction was performed in a 300 mL autoclave using 0.1 mol of the substrate in 15 mL of THF.
[c]3-nonen-1-ol/1-nonanol = 90/10 ratio.
[d]10-undecen-1-ol/1-undecanol = 82/11 ratio.
[e]10-undecen-1-ol/1-undecanol = 63/24.
[f]10-undecen-1-ol/1-undecanol = 63/13.
[g]E,E-9,12-octadecadien-1-ol/E,Z-9,11-octadecadien-1-ol/Z,E-10,12-octadecadien-1-ol = 57/22/21

Example 16

Typical Procedure for Hydrogenation of Enals, Enones, Enolates with Complexes (1)-(4)

For all experiments, conversions were determined by $^1H$ NMR spectroscopy using ca. 0.65 mL samples taken from reactions mixtures without dilution or mixing with other solvents. Spectra were collected without $^2H$ lock, using 0.3 μs $^1H$ pulses and a 10 s acquisition time to ensure accurate integration of the peaks.

In an argon glovebox, the required amount of complexes 4-6, and a solvent (THF or iPrOH, 7 mL for Parr 75 mL and 50 mL for Parr 300 mL) was added to the desired amount of base (tBuOK, NaOMe, $Na_2CO_3$, $K_2CO_3$ or $Cs_2CO_3$). The obtained mixture was then mixed with the substrate (0.02-0.10 mol) and transferred into a stainless-steel Parr reactor (75 mL or 300 mL) equipped with a magnetic stir bar. The reactor was closed, taken out of the glovebox, tightened and connected to a hydrogen tank. After purging the line, the reactor was pressurized to 725 psi (50 Bar) and disconnected from the $H_2$ source. Then, the reactor was placed in an oil bath preheated to 100'C. At the end of the reaction time, the reactor was moved into a cold water bath for 5 min and depressurized.

Table 4 below outlines comparative results between complexes (1)-(4) and complexes (I)-(V) for methyl 10-undecenoate hydrogenation. Table 5 below outlines the results of enal, enone, and enolate hydrogenations with complex (1b) (see FIGS. 5-7).

TABLE 4

Comparative hydrogenation of methyl undec-10-enoate with catalysts I-V and 1-4.[a]

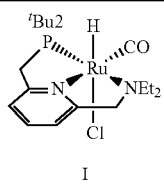

I

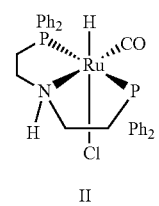

II

TABLE 4-continued

Comparative hydrogenation of methyl undec-10-enoate with catalysts I-V and 1-4.[a]

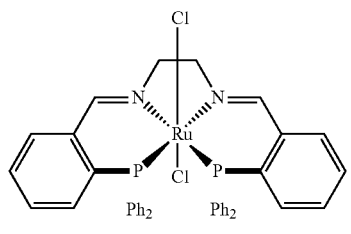

III

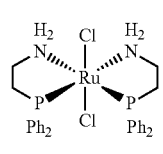

IV

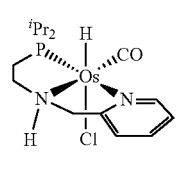

V

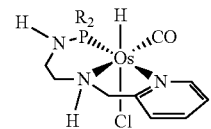

1a-c, R = $^iPr$, $^tBu$, Ad

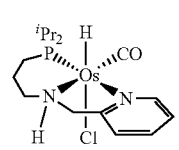

2

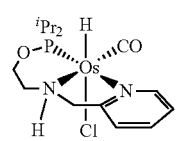

TABLE 4-continued

Comparative hydrogenation of methyl undec-10-enoate with catalysts I-V and 1-4.[a]

3

[Structure of catalyst 3]

4

[Reaction scheme: methyl undec-10-enoate + H₂, [cat] → RCH₂OH + R'C(O)OCH₂R + MeOH]

| Catalyst | Conversion, %[b] | C=C retention, %[c] | C-9 olefins, %[d] |
|---|---|---|---|
| I | 77 | 10 | 100 |
| II | 18 | 89 | 3 |
| III[e] | 100 | 36 | —[f] |
| IV | 70 | 22 | 39 |
| V | 62 | 79 | 3 |
| 1a | 96 | 91 | <1 |
| 1b | 98 | 94 | <1 |
| 1c | 93 | 94 | <1 |
| 2 | 40 | 92 | <1 |
| 3 | 5 | 85 | 1 |
| 4 | 92 | 34 | 63 |

R = [structures of various alkenyl/alkyl groups with subscript 5]

or or or

[a]reaction time 2.5 h at 100° C., using 0.1 mol of ester, 0.05 mol % catalyst, 1 mol % ᵗBuOK in 7 mL of THF; p(H₂) = 50 bar. Complex 2 was previously disclosed in PCT/CA2012-050571.
[b]Total conversion to undec-10-enol and undecanol.
[c]100% when no C=C bond hydrogenation.
[d]The percentage of C-9 olefins, as 100 × [C-9] / ([C-9] + [C-10]).
[e]with 5 mol % NaOMe, data from [L. A. Saudan, C. M. Saudan, C. Debieux, P. Wyss, *Angew. Chem. Inter. Ed.* 2007, 119, 7617-7620]
[f]have not been determined in [L. A. Saudan, C. M. Saudan, C. Debieux, P. Wyss, *Angew. Chem. Inter. Ed.* 2007, 119, 7617-7620.]

TABLE 5

Figure 5:
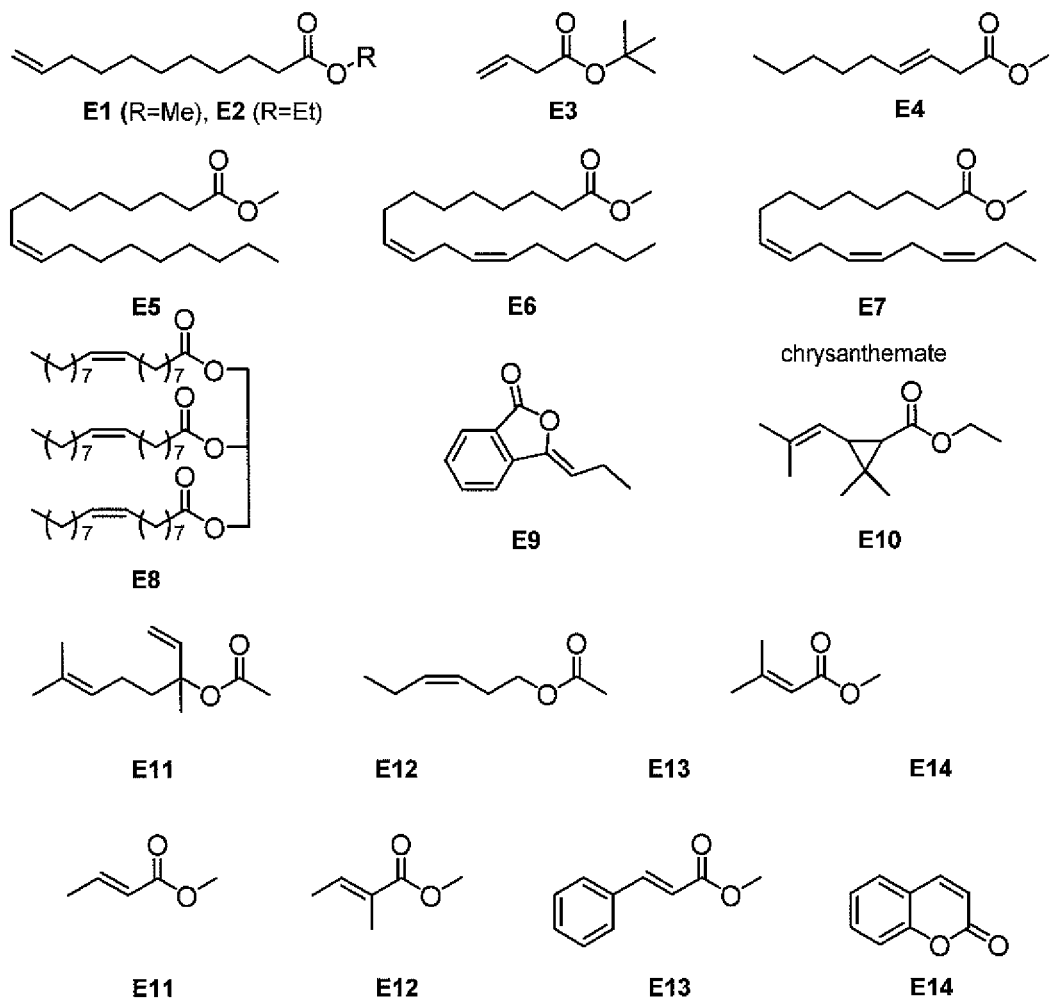
FIG. 5 depicts a series of viable substrates for enolate hydrogenation by complexes disclosed herein.
Figure 6:
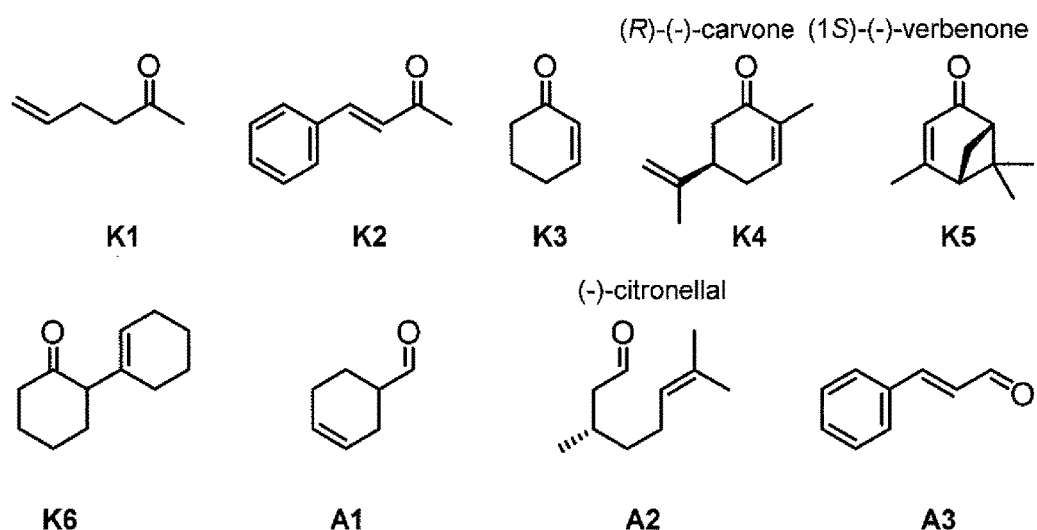
FIG. 6 depicts a series of viable substrates for enal and enone hydrogenation by complexes disclosed herein.

Hydrogenation of substrates (S) of FIGS. 5 and 6 with Complex 1b.[a]

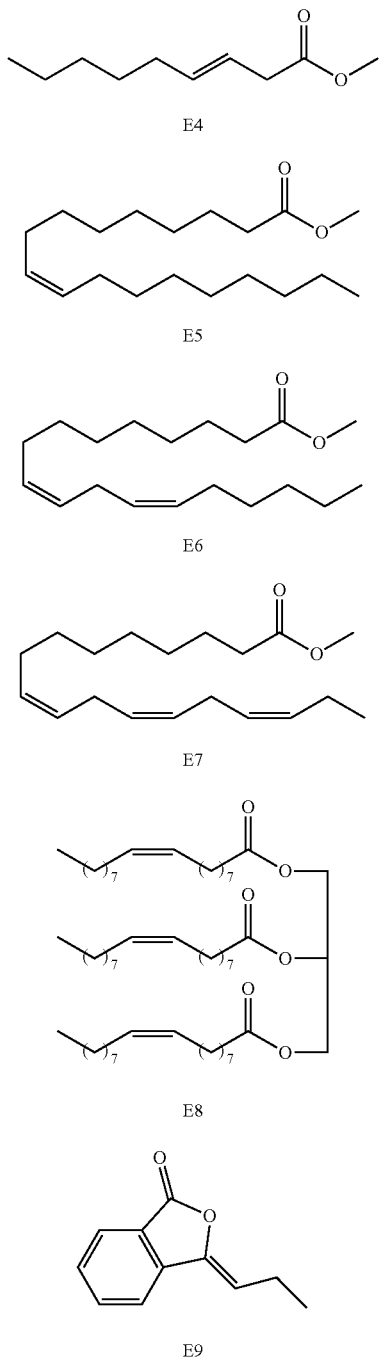

E1 (R = Me), E2 (R = Et)

E3

E4

E5

E6

E7

E8

E9 chrysanthemate

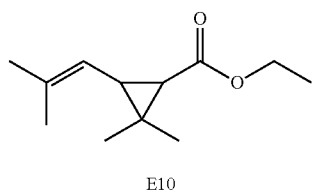

E10

TABLE 5-continued
Hydrogenation of substrates (S) of FIGS. 5 and 6 with Complex 1b.[a]
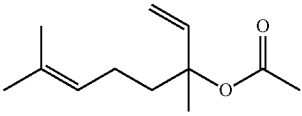
E11
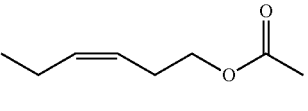
E12
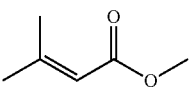
E13
E11
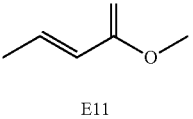
E12
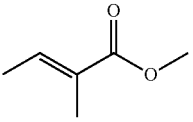
E13
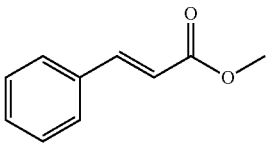
E14
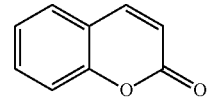 [SMILES: O=c1ccc2ccccc2o1]
K1
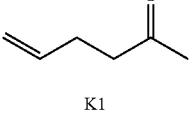
K2
TABLE 5-continued
Hydrogenation of substrates (S) of FIGS. 5 and 6 with Complex 1b.[a]
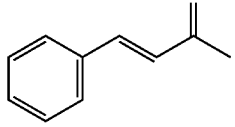
K3
(R)-(−)-carvone
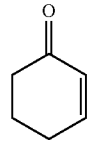
K4
(1S)-(−)-verbenone
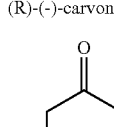
K5
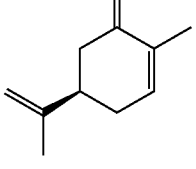
K6
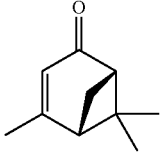
A1
(−)-citronellal
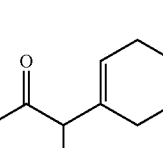
A2
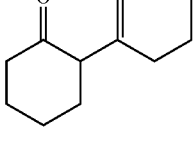
A3

TABLE 5-continued

Hydrogenation of substrates (S) of FIGS. 5 and 6 with Complex 1b.[a]

| S | [Cat][b] | t, h | Solv. | Base[c] | T, °C. | Sel.[d] | Conv[e] |
|---|---|---|---|---|---|---|---|
| E1 | 0.01 | 5 | neat | NaOMe, 2 | 100 | 98 | 98 |
| E2 | 0.01 | 4 | neat | NaOMe, 2 | 100 | 96 | 97 |
| E5 | 0.01 | 4 | neat | NaOMe, 2 | 100 | 100 | 98 |
| E6 | 0.05 | 3 | neat | $Cs_2CO_3$, 1.5 | 100 | 100 | 98 |
| E7 | 0.05 | 3 | neat | $Cs_2CO_3$, 1.5 | 100 | 100 | >99 |
| K1 | 0.05 | 2 | THF | tBuOK, 0.25 | 23 | 100 | 100 |
| K2 | 0.01 | 12 | iPrOH | $Na_2CO_3$, 1 | 23 | 98 | 100 |
| K3 | 0.015 | 2 | THF | $Na_2CO_3$, 1 | 100 | 92 | 100 |
| K4 | 0.01 | 9 | THF | $Na_2CO_3$, 1 | 100 | 100 | 99 |
| K5 | 0.05 | 12 | iPrOH | $Na_2CO_3$, 1 | 100 | 100 | 100 |
| A1 | 0.05 | 3 | THF | $K_2CO_3$, 3 | 100 | 100 | 100 |
| A2 | 0.05 | 2 | THF | $Cs_2CO_3$, 1 | 100 | 100 | 100 |
| A3 | 0.05 | 2.5 | THF | $K_2CO_3$, 1 | 80 | >99 | >99 |

[a]Unless mentioned otherwise, 0.02 mol of substrate in 7 mL of solvent was hydrogenated in a 75 mL Parr high-pressure vessel.
[b]Catalyst, mol %.
[c]Base, mol %.
[d]Selectivity (100% when no C═C bond hydrogenation).
[e]Total (saturated + unsaturated) conversion to alcohol determined by quantitative integration of the NMR spectra.
[d]Hydrogenation in a 300 mL Parr autoclave.

DISCUSSION

Figure 2:
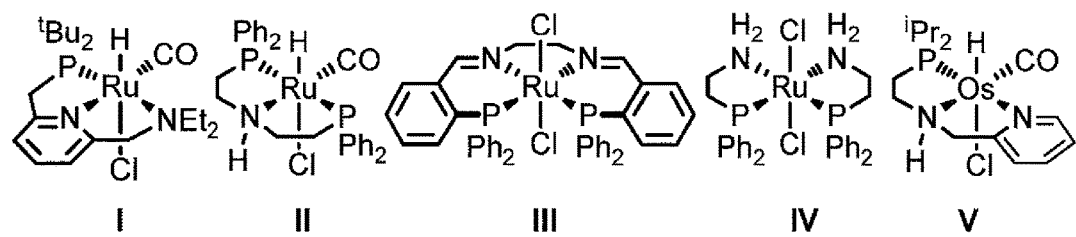
FIG. 2 depicts currently best-known homogeneous ester hydrogenation catalysts.

As discussed above, chemo selectivity is difficult to achieve in ester/enolate hydrogenation; few efficient catalysts are known, and those that are known have only become available recently. Hydrogenation of methyl 10-undecenoate, a chemical derived from castor oil, was investigated with currently available catalysts (I-V) and those disclosed herein (1, 3, 4). 10-Undecenol, considered the most desirable product of methyl 10-undecenoate hydrogenation, is a valuable material for perfumery products and polymeric compounds. Results of hydrogenation of methyl 10-undecenoate using hydrogenation catalysts I-V (see FIG. 2) are outlined in Table 4. 10-undecenol's vinyl group was readily identified in reaction mixtures by NMR. Hydrogenation of the C═C bond gave rise to $^1$H and $^{13}$C methyl resonances at δ 0.89 and 14.1 ppm, respectively, whereas the 9-ene products exhibited distinct $^{13}$C shifts at δ 12.6, 123.7, 131.0 (Z) and 17.8, 124.8, 131.9 (E).

It was found that industrial catalysts II (Ru-MACHO, Takasago), III and IV (Firmenich) hydrogenate C═O and C═C bonds of methyl 10-undecenoate at similar rates. C-10 to C-9 C═C bond migration was also a problem. Milstein's catalyst I afforded mostly saturated products (see Table 4), with no 10-undecenol. Performance of osmium catalyst V was also unsatisfactory.

Complexes 1-4 (see Table 4) were based on NNXP-R═PyCHNHC$_2$H$_4$XPR$_2$ ligand systems (X═NH, CH$_2$, O). Of complexes 1-4, NNNP-tBu complex 1b emerged as the most successful catalyst for 10-undecenoate reduction: its hydrogenation rate and selectivity increased further without solvent. Thus, with a substrate to catalyst ratio of $10^4$ (8 g of neat methyl 10-undecenoate and 2.2 mg of 1b), hydrogenation was quantitative in 5 h, in 98% selectivity (see Table 5, E1).

Consequently, complex 1b, was further tested on a large group of challenging substrates, while varying the reaction temperature, solvent, base, and time (see Table 5, FIGS. 5 and 6). It was established that 1b is a robust, practical, highly efficient $H_2$ hydrogenation catalyst with excellent carbonyl selectivity.

Figure 7:
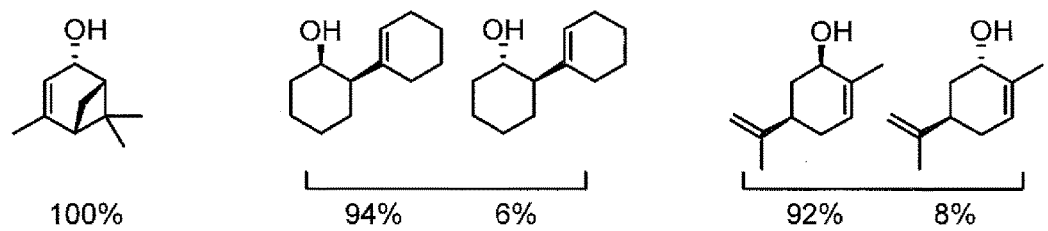
FIG. 7 depicts chemo- and stereoselective hydrogenations of enone substrates by complexes disclosed herein.

Complex 1b also demonstrated stereoselectivity for certain substrates, specifically K4, K5, and K6 (see FIGS. 6 and 7). Without being bound by theory, it was postulated that such stereoselectivity resulted from one face of complex 1b being more sterically hindered than the other, resulting in substrates preferentially interacting with the least sterically hindered side, generating stereoselective products. This demonstrated that the complexes disclosed herein could effectively generate stereoselective hydrogenation products.

Complexes of formula (6) and (7) (shown below, wherein $R^1$═iPr) were synthesized via the general methods described above. Complex (6) demonstrated similar activity and/or regioselectivity as complexes (1a-c), (3), and (4) in ester, ketone, enal, enone, enoate, plant and seed oil, ester with multiple ester groups, and imine group hydrogenations. Complex (7) did not display similar regioselectivity in enal, enone, enoate hydrogenations as complexes (1a-c), (3), and (4).

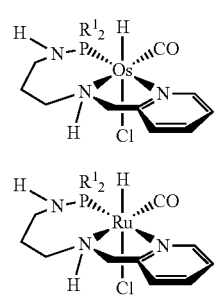

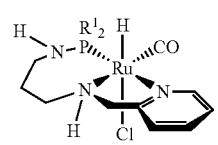

Example 17

Transesterification and Hydrogenation of Tung Oil

Figure 4:
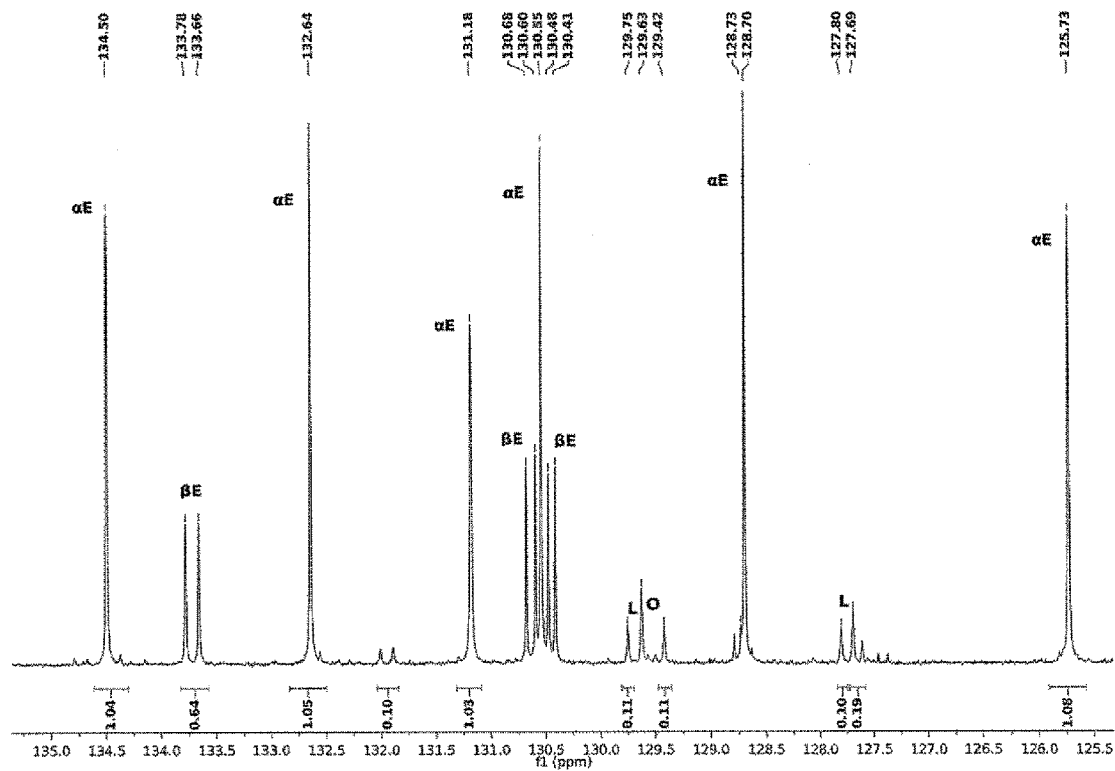
FIG. 4 depicts Tung Oil trans-esterification products, and an associated $^{13}C$ NMR spectrum.
Figure 4:
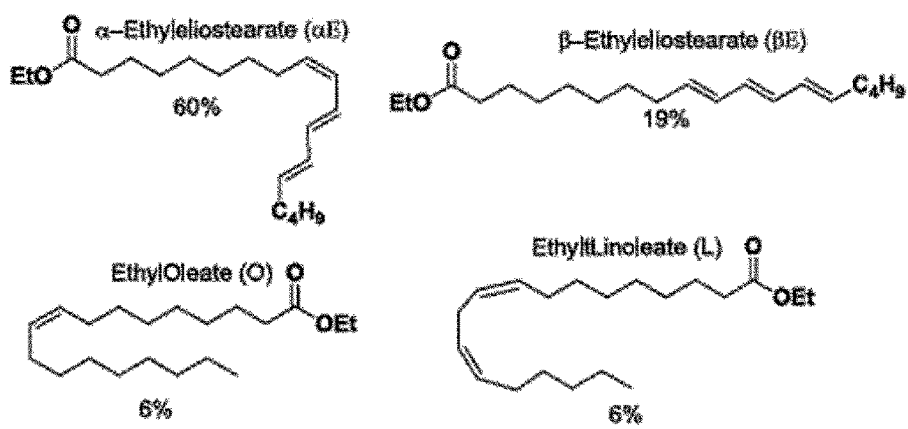

To a 250 mL round bottom flask containing 100 g (~0.114 mol) of tung oil (from natural sources) was added a solution of KOH (300 mg) in 50 mL of ethanol. The resulting mixture was vigorously stirred and heated at 90° C. for 1 h. After that time, 200 mL of hexanes were added and a subsequently obtained extract was washed with 3×100 mL of $Na_2CO_3$ (5 w %) in water. The organic layer was dried over $MgSO_4$ for 2 h, filtered through 5 cm×3 cm layer of $Al_2O_3$, and hexanes were removed in vacuo. The mixture of ethyl esters was isolated as a pale yellow oil 67 g (64%). Its composition was determined by NMR spectroscopy (see FIG. 4).

Example 18

Hydrogenation of Tung Oil and Coconut Oil with Complex 1a

A THF solution of complex 1a (14 mg or 32 mg, 50 mL) was added to tBuOK (67 mg or 197 mg for $Cs_2CO_3$, 3 mol %). The resulting mixture was stirred for 1-2 min and then coconut (or tung) oil (0.02 mol) was added. The mixture was then transferred into a 300 mL stainless-steel reactor (Parr) equipped with a magnetic stir bar. The reactor was purged by two cycles of pressurization/venting with $H_2$ (150 psi, 10 Bar) and then pressurized with $H_2$ (725 psi, 50 Bar) and disconnected from the $H_2$ source. The reaction was conducted at 100° C. At the end of a required amount of reaction time, the reactor was placed into a cold water bath, and was depressurized after cooling to the ambient temperature. See Table 6 for results.

TABLE 6

Hydrogenation of coconut and tung oils using complex 1a.

| Substrate | Substrate/Catalyst Ratio | t, h | Solvent | Base, mol % | T, °C | Conv. (%) |
|---|---|---|---|---|---|---|
| Coconut Oil | 750 | 14 | THF | tBuOK, 3 | 100 | 95[a] |
| Tung Oil | 333 | 16 | THF | Cs$_2$CO$_3$, 3 | 100 | 49[bc] |

[a] Conversion denotes amount of fatty acid converted to alcohol; no C=C hydrogenation was observed.
[b] Conversion denotes amount of fatty acid converted to alcohol.
[c] Due to tung oil being mixtures of many fatty acids, selectivity was not calculated.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compound of Formula A or Formula Ic

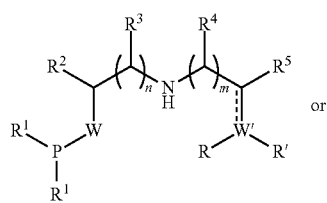

Formula A

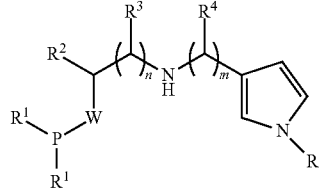

Formula Ic wherein
each R$^1$, R$^2$, R$^3$, and R$^4$ are each independently H, a substituted or unsubstituted linear or branched C$_1$-C$_{12}$ alkyl, a substituted or unsubstituted cyclic C$_3$-C$_{12}$ alkyl, a substituted or unsubstituted C$_3$-C$_{12}$ alkenyl, or a substituted or unsubstituted aryl or heteroaryl group, or when taken together with the atoms to which they are attached, any two of the R$^2$, R$^3$, R$^4$ groups form an optionally substituted saturated or partially saturated cycloalkyl, or an optionally substituted aryl or heteroaryl;
W is an oxygen atom or an NH group;
W' is an oxygen atom or a nitrogen atom;
the dashed line is either present and denotes the presence of one bond of a double bond or is absent;
R is absent, H, a substituted or unsubstituted linear or branched C$_1$-C$_{12}$ alkyl, a substituted or unsubstituted cyclic C$_3$-C$_{12}$ alkyl, a substituted or unsubstituted C$_3$-C$_{12}$ alkenyl, or a substituted or unsubstituted aryl or heteroaryl group;
R', when taken together with R$^5$ and the atoms to which they are attached forms a substituted or unsubstituted pyridyl, furanyl, imidazolyl, pyrazolyl or oxazolyl;
n and m are each independently an integer 1 or 2;
wherein:
an aryl group comprises from 6 to 50 carbon atoms;
a heteroaryl group comprises from 4 to 8 carbon atoms in addition to at least one heteroatom selected from the group consisting of O, S and N.

2. The compound of claim 1, wherein:
the compound has the structure of Formula Ia, Ib, or Ic,

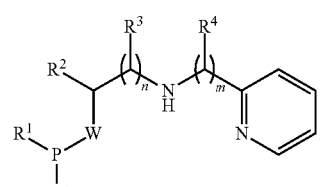

Formula Ia

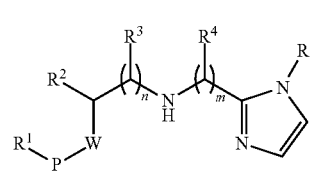

Formula Ib

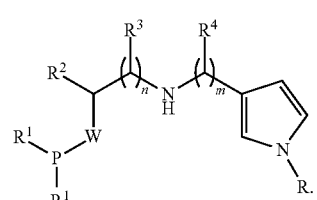

Formula Ic

3. The compound of claim 1, wherein:
(a) n is 1, or m is 1 or both n and m are 1; or
(b) the compound has the structure of Formula I

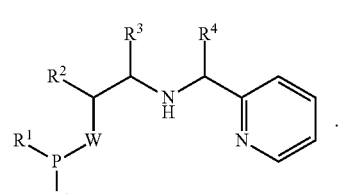

Formula I

4. A metal complex of Formula IV $$M(PWNN)X_kY \quad [IV]$$

wherein M is a transition metal;
each X represents simultaneously or independently a hydrogen or a halogen atom, a C$_1$-C$_5$ alkyl radical, a hydroxyl group, or a C$_1$-C$_7$ alkoxy radical;
Y is CO, NO, carbene, isonitrile, nitrile, phosphite, phosphinite, or a phosphine, such as PMe$_3$, PPh$_3$, PCy$_3$, P(iPr)$_3$;
k is an integer 1 or 2; and PWNN is a ligand represented by Formula A or Formula Ic

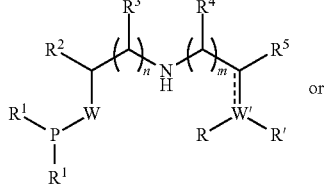

Formula A or

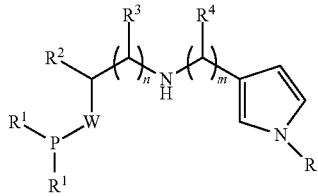

Formula Ic wherein
each $R^1$, $R^2$, $R^3$, and $R^4$ are each independently H, a substituted or unsubstituted linear or branched $C_1$-$C_{12}$ alkyl, a substituted or unsubstituted cyclic $C_3$-$C_{12}$ alkyl, a substituted or unsubstituted $C_3$-$C_{12}$ alkenyl, or a substituted or unsubstituted aryl or heteroaryl group, or when taken together with the atoms to which they are attached, any two of the $R^2$, $R^3$, $R^4$ groups form an optionally substituted saturated or partially saturated cycloalkyl, or an optionally substituted aryl or heteroaryl;
W is an oxygen atom or an NH group;
W' is an oxygen or a nitrogen atom;
the dashed line is either present and denotes the presence of one bond of a double bond or is absent;
R is absent, H, a substituted or unsubstituted linear or branched $C_1$-$C_{12}$ alkyl, a substituted or unsubstituted cyclic $C_3$-$C_{12}$ alkyl, a substituted or unsubstituted $C_3$-$C_{12}$ alkenyl, or a substituted or unsubstituted aryl or heteroaryl group;
R', when taken together with $R^5$ and the atoms to which they are attached forms a substituted or unsubstituted pyridyl, furanyl, imidazolyl, pyrazolyl or oxazolyl; and
n and m are each independently an integer 1 or 2;
wherein the metal complex of Formula IV is either neutral or cationic;
wherein:
an aryl group comprises from 6 to 50 carbon atoms;
a heteroaryl group comprises from 4 to 8 carbon atoms in addition to at least one heteroatom selected from the group consisting of O, S and N.

5. The metal complex of claim 4, which comprises the PWNN ligand, wherein:
the PWNN ligand has the structure of Formula Ia, Ib, or Ic,

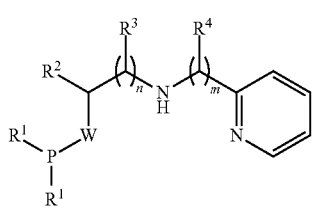

Formula Ia

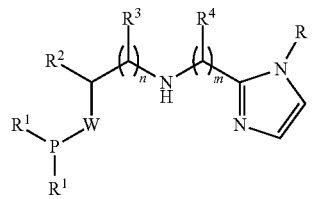

Formula Ib

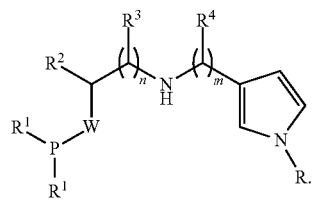

Formula Ic

6. The metal complex of claim 4, wherein:
(a) n is 1, or m is 1 or both n and m are 1; or
(b) the ligand is a PWNN Ligand having the structure of Formula I

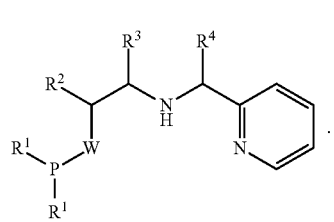

Formula I

7. The metal complex of claim 4, wherein M is:
(a) a group 7 (manganese group) metal, a group 8 (iron group) metal, group 9 (cobalt group) metal, or group 10 (nickel group) metal; or
(b) Ru or Os.

8. The metal complex of claim 4, which is:

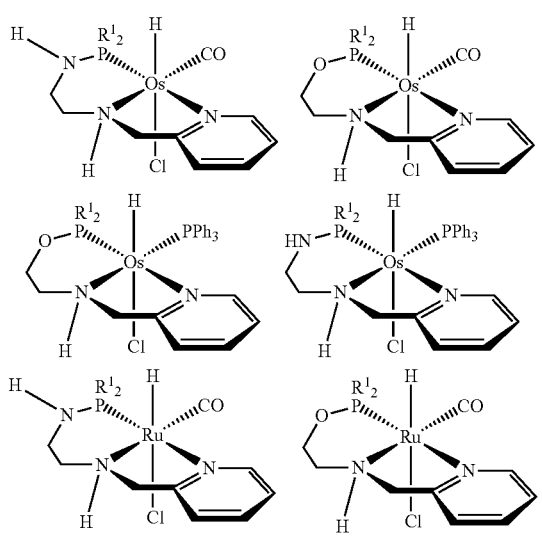

-continued

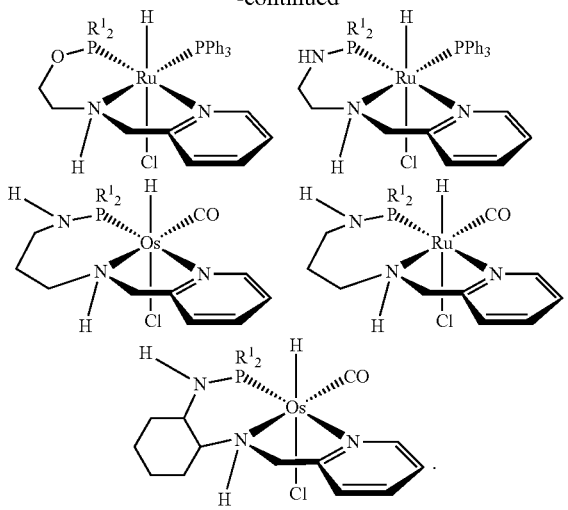

9. A process for dehydrogenation of a substrate, comprising treating the substrate with a catalytic amount of a metal complex of claim 4.

10. The process of claim 9, wherein:
(a) the substrate is treated with the catalytic amount of the metal complex in the presence of a base, a solvent or both; or
(b) the treating step is performed at a reaction temperature between about 0° C. and about 250° C. or between about 50° C. and about 150° C., or between about 50° C. and about 100° C., or between about 50° C. and about 75° C.

11. The process of claim 9, wherein:
(a) the substrate has at least one alcohol moiety; or
(b) the substrate is a compound of the following formula:

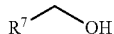

wherein $R^7$ is a substituted or unsubstituted alkyl; a substituted or unsubstituted aryl; or
$R^7$ comprises an amino group that undergoes dehydrogenation.

12. The process of claim 9, wherein:
(a) the catalytic amount of metal complex is between 10-1000 pm, or between 10-500 ppm, or between 10-250 ppm, or between 10-100 ppm, or between 10-50 ppm;
(b) the substrate comprises more than one hydroxyl moiety that undergoes dehydrogenation; or
(c) the substrate and product pair of the dehydrogenation reaction is selected from the group consisting of:

| Substrate | Product |
|---|---|
| Alcohols | ester |
| Alcohol | aldehyde |
| Alcohol | ketone |
| Diol | lactone |
| amine + alcohol | amide |
| amine + alcohol | substituted amine |
| amine + alcohol | imine |
| ammonia-borane | aminoboranes |
| ammonia-borane | borazine |
| Amine | imine |

-continued

| Substrate | Product |
|---|---|
| Amines | guanidine |
| alcohol + thiol | thioester |
| Thiol | sulphoxide |
| alcohol + phosphine | acyl phosphine. |

13. The process of claim 9 for producing $H_2$.

14. A process for producing $H_2$ comprising dehydrogenating a substrate by treating the substrate with a catalytic amount of the metal complex of claim 4.

15. The process of claim 14, wherein:
(a) the substrate comprises an alcohol or amine or wherein the substrate is ammonia-borane;
(b) the process does not require a hydrogen acceptor, and/or
(c) the process is a homogeneous process.

16. A process for hydrogenation of a substrate comprising treating the substrate under a pressure of hydrogen with a catalytic amount of a metal complex of claim 4.

17. The process of claim 16, wherein:
(a) the substrate is treated with the catalytic amount of the metal complex in the presence of a base, a solvent or both;
(b) the treating step is performed at a reaction temperature between about 0° C. and about 200° C., or between about 20° C. and about 100° C., or between about 20° C. and about 75° C., or between about 20° and about 50° C.; and/or
(c) the substrate has at least one ester, enal, enone, or enolate moiety.

18. The process of claim 16, which proceeds according to one of the following schemes:

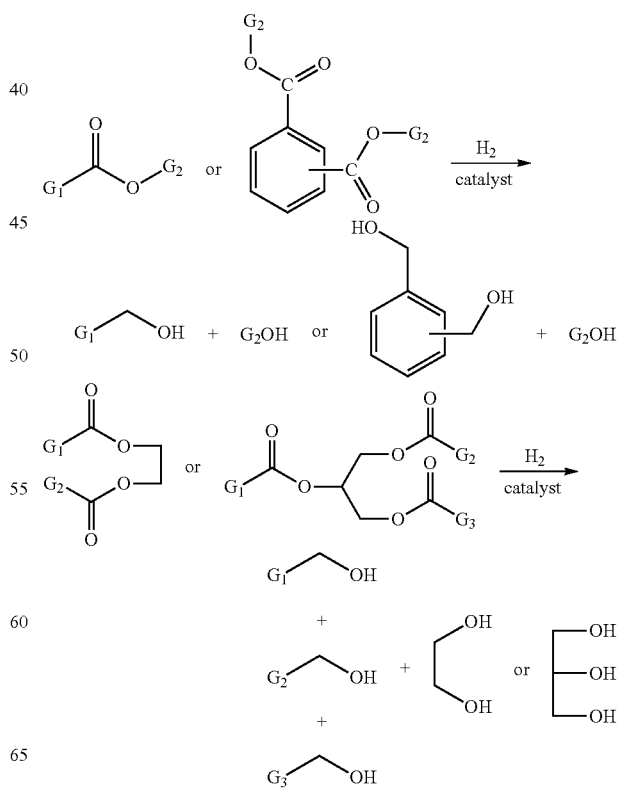

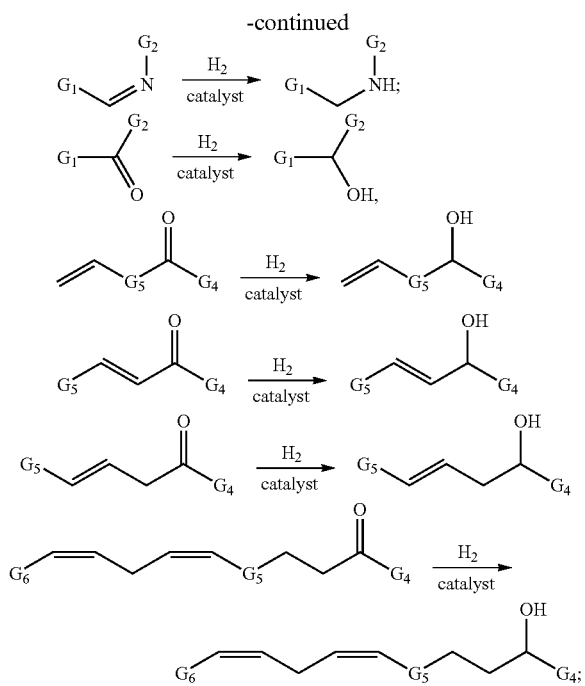

wherein groups $G_1$, $G_2$, $G_3$, $G_4$, $G_5$ and $G_6$ simultaneously or independently, represent a linear, branched $C_1$-$C_{40}$ or cyclic $C_3$-$C_{40}$ alkyl, alkenyl or aromatic group, optionally substituted.

19. The process of claim 16, wherein:
(a) the catalytic amount of metal complex is between about 10 and about 1000 pm, or between about 10 and about 500 ppm, or between about 10 and about 250 ppm, or between about 10 and about 100 ppm, or between about 10 and about 50 ppm;
(b) the hydrogen pressure is between about 1 and about 200 bar, or between about 1 and about 150 bar, or between about 1 and about 100 bar, or between about 1 and about 70 bar, or between about 1 and about 50 bar;
(c) the hydrogenation proceeds regioselectively, chemoselectively, and/or stereoselectively; and/or
(d) the substrate and product pair of the hydrogenation reaction is selected from the group consisting of:

| Hydrogenation Substrate | Product |
|---|---|
| Aldehyde | alcohol |
| Ketone | alcohol |
| Ester | alcohol |
| carboxylic acid | alcohol |
| Ketene | alcohol |
| Enol | alcohol |
| Epoxide | alcohol |
| Aldimine | amine |
| Ketamine | amine |
| ketene-imine | amine |
| Nitrile | amine |
| Aziridine | amine |
| Nitro | amine |
| Diazo | amine |
| Isocyanide | amine |
| Enamine | amine |
| Lactone | diol |
| Amide | amine + alcohol |
| Aminoboranes | amine-borane |
| Borazine | amine-borane |
| Olefin | alkane |
| Acetylene | alkane |
| Allene | alkane. |

20. The process of claim 9, wherein the process is performed in the absence of solvent, base or both.

21. The process of claim 14, wherein the process is performed in the absence of a solvent, base or both.

22. The process of claim 16, wherein the process is performed in the absence of a solvent, base or both.

* * * * *